(12) United States Patent
Schauer et al.

(10) Patent No.: US 12,329,990 B2
(45) Date of Patent: Jun. 17, 2025

(54) MATCHED FILTER IN IONOACOUSTIC SIGNAL PROCESSING FOR ION BEAM RANGE DETERMINATION AND DOSIMETRY

(71) Applicants: Universität der Bundeswehr München, Neubiberg (DE); Technische Universität München, Munich (DE); Ludwig-Maximilians-Universität München, Munich (DE)

(72) Inventors: Jannis Schauer, Munich (DE); Günther Dollinger, Garching (DE); Heinrich Ruser, Munich (DE); Yuanhui Huang, Eching (DE); Vasilis Ntziachristos, Munich (DE); Hans Peter Wieser, Munich (DE); Katia Parodi, Munich (DE)

(73) Assignees: Universität der Bundeswehr München, Neubiberg (DE); Technische Universität München, Munich (DE); Ludwig-Maximilians-Universität München, Munich (DE)

( * ) Notice: Subject to any disclaimer, the term of this patent is extended or adjusted under 35 U.S.C. 154(b) by 148 days.

(21) Appl. No.: 18/176,047

(22) Filed: Feb. 28, 2023

(65) Prior Publication Data
US 2023/0277875 A1 Sep. 7, 2023

(30) Foreign Application Priority Data
Mar. 3, 2022 (EP) .................................. 22159975

(51) Int. Cl.
*A61N 5/10* (2006.01)
*A61B 8/00* (2006.01)

(52) U.S. Cl.
CPC .......... *A61N 5/1071* (2013.01); *A61B 8/4488* (2013.01); *A61N 2005/1041* (2013.01); *A61N 2005/1087* (2013.01)

(58) Field of Classification Search
CPC .......... A61N 5/1071; A61N 2005/1041; A61N 2005/1087; A61B 8/4488
See application file for complete search history.

(56) References Cited

U.S. PATENT DOCUMENTS 11,143,628 B2 * 10/2021 Tillotson .............. G01N 29/223
2008/0217561 A1 * 9/2008 Mackie ................ A61N 5/1075
250/491.1

(Continued)

FOREIGN PATENT DOCUMENTS

WO 2016009042 A1 1/2016
WO 2018022431 A1 2/2018

OTHER PUBLICATIONS

Haffa, Daniel, et al. "I-BEAT: Ultrasonic method for online measurement of the energy distribution of a single ion bunch." Scientific reports 9.1 (2019): 6714. (Year: 2019).*

(Continued)

*Primary Examiner* — Sean D Mattson
(74) *Attorney, Agent, or Firm* — Grossman, Tucker, Perreault & Pfleger, PLLC

(57) ABSTRACT

A method and an apparatus for determining information regarding the location of energy deposition of an ion beam, in particular a proton beam, in an absorptive medium, such as in the tissue of a patient undergoing radiation therapy.

20 Claims, 14 Drawing Sheets

(56) References Cited

U.S. PATENT DOCUMENTS

| | | | |
|---|---|---|---|
| 2016/0074675 A1* | 3/2016 | Moskvin | A61B 8/483 600/1 |
| 2017/0165504 A1* | 6/2017 | Dollinger | A61N 5/1048 |
| 2019/0175947 A1* | 6/2019 | Patch | A61N 5/1067 |

OTHER PUBLICATIONS

Freijo, Clara, et al. "Dictionary-based protoacoustic dose map imaging for proton range verification." Photoacoustics 21 (2021): 100240. (Year: 2021).*

Assmann et al., "Ionoacoustic characterization of the proton Bragg peak with submillimeter accuracy", Medical Physics, vol. 42, No. 2, 2015, Germany, pp. 567-574.

Boehlen et al., "The FLUKA Code: Developments and Challenges for High Energy and Medical Applications", Nuclear Data Sheets, vol. 120, 2014, Switzerland, pp. 211-214.

Ferrari et al., "FLUKA: A Multi-Particle Transport Code", European Organization for Nuclear Research, 2005, California, pp. 1-387.

Hayakawa et al., "Acoustic Pulse Generated in a Patient During Treatment by Pulsed Proton Radiation Beam", Radiation Oncology Investigations, vol. 3, 1995, Japan, pp. 42-45.

Hueso-Gonzalez et al., "A full-scale clinical prototype for proton range verification using prompt gamma-ray spectroscopy", Physics In Medicine and Biology, 2018, Massachussetts, pp. 1-33.

Johnson et al., "Review of medical radiography and tomography with proton beams", Reports on Progress in Physics, 2017, California, pp. 1-44.

Krimmer et al., "Prompt-gamma monitoring in hadrontherapy: a review", Nuclear Instruments & Methods in Physics Research, 2017, France, pp. 1-70.

Lehrack et al., "Submillimeter ionoacoustic range determination for protons in water at a clinical synchrocyclotron", Physics in Medicine & Biology, vol. 62, 2017, Germany, pp. L20-L30.

Lomax et al., "A treatment planning inter-comparison of proton and intensity modulated photon radiotherapy", Radiotherapy & Oncology, vol. 51, 1999, Switzerland, pp. 257-271.

Parodi et al., "In vivo range verification in particle therapy", Med. Physics, vol. 45, No. 11, 2018, Germany, pp. 1036-1050.

Tada et al., "Time resolved properties of acoustic pulses generated in water and in soft tissue by pulsed proton beam irradiation—A possibility of doses distribution monitoring in proton radiation therapy", Medical Physics, vol. 18, No. 6, 1991, Japan, pp. 1100-1104.

Turin, "An Introduction to Matched Filters", IRE Transactions on Information Theory, 1960, pp. 311-329.

Unkelbach et al., "Robust radiotherapy planning", 2018, Germany, pp. 1-47.

Zhu et al., "Proton Therapy Verification with PET Imaging", Theranostics, vol. 3, Issue 10, 2013, Massachusetts, pp. 731-740.

Caron, et al., "Single pulse protoacoustic range verification using a clinical synchrocyclotron", Phys Med Biol. 68(4), Author manuscript, HHS Public Access, available in PMC Oct. 11, 2023, pp. 1-17.

Girst, Stefanie "Proton Minibeam Radiotherapy", Universitaet der Bundeswehr Muenchen, Neubiberg (Germany). Fakultaet fuer Luft- und Raumfahrttechnik, 2016, 149 pages.

Jones, et al., "Acoustic-Based Proton Range Verification in Heterogeneous Tissue: Simulation Studies", Physics in Medicine and Biology, Institute of Physics and Engineering in Medicine, Accepted Manuscript, 2017, pp. 1-38.

Jones, et al., "How Proton Pulse Characteristics Influence Protoacoustic Determination of Proton-Beam Range: Simulation Studies", Physics in Medicine & Biology, Institute of Physics and Engineering in Medicine 61, 2016, pp. 2213-2242.

Lehrack, et al., "Ionoacoustic Detection of Swift Heavy Ions", Nuclear Instruments and Methods in Physics Research Section A: Accelerators, Spectrometers, Detectors and Associated Equipment, vol. 950, 2020, 22 pages.

Patch, et al., "Thermoacoustic Range Verification During Pencil Beam Delivery of a Clinical Plan to an Abdominal Imaging Phantom", Radiotherapy and Oncology, vol. 159, 2021, Elsevier, pp. 224-230.

Patch, et al., "Thermoacoustic Range Verification in the Presence of Acoustic Heterogeneity and Soundspeed Errors—Robustness Relative to Ultrasound Image of Underlying Anatomy", Medical Physics, vol. 46, No. 1, Nov. 23, 2018, pp. 318-327.

Patch, et al., "Thermoacoustic Range Verification Using a Clinical Ultrasound Array Provides Perfectly Co-Registered Overlay of the Bragg Peak Onto an Ultrasound Image", Physics in Medicine & Biology, Institute of Physics and Engineering in Medicine, vol. 61, No. 5621, 2016, pp. 1-28.

Vallicelli, et al., "Denoising for Enhancing Signal-to-Noise Ratio in Proton Sound Detectors", 2021 IEEE Biomedical Circuits and Systems Conference (BioCAS), Berlin, Germany, 2021, pp. 1-4.

Extended European Search Report of European Application No. 22159975.6, Dated Aug. 25, 2022, 8 pages.

Sebastian Lehrack et al: "Submillimeter ionoacoustic range determination for protons in water at a clinical synchrocyclotron", Physics in Medicine and Biology, Institute of Physics Publishing, Bristol, GB, vol. 62, No. 17.

Freijo Clara et al: "Dictionary-based protoacoustic dose map imaging for proton range verification", Photoacoustics, vol. 21, Mar. 1, 2021, p. 100240.

* cited by examiner

MATCHED FILTER IN IONOACOUSTIC SIGNAL PROCESSING FOR ION BEAM RANGE DETERMINATION AND DOSIMETRY

FIELD OF THE INVENTION

While not strictly limited to medical sciences, the present invention finds particular use in the field of radiation therapy. More precisely, the invention relates to a method and an apparatus for determining information regarding the location of energy deposition of an ion beam, in particular a proton beam, in an absorptive medium, such as in the tissue of a patient undergoing radiation therapy.

BACKGROUND OF THE INVENTION

In radiation therapy, ionizing radiation is used for medical purposes, in particular as part of cancer treatment to control or kill malignant cells. The most common type of radiation therapy is based on x-ray photons. MeV photons can be generated with moderate effort using for example a linear accelerator for accelerating an electron beam that is directed to a target to generate x-ray radiation as Bremsstrahlung. However, in x-ray radiation therapy, one always has to cope with the problem that the dose cannot be confined to the tumor area, but also affects healthy tissue. Part of this problem is due to the fact that the energy deposition of an x-ray beam in human tissue decreases nearly exponentially along the penetration depth and that the x-ray radiation will also affect healthy tissue in front of and behind the target area, since the x-rays are typically applied from outside the human body.

In contrast to this, using ion beams, such as protons, helium ions, boron ions, carbon ions or neon ions, the damage to healthy tissue can be significantly reduced. To appreciate this, reference is made to FIG. 1, where the energy deposition or dose of 10 MeV photons as a function of penetration depth is compared with that of several proton beams of different energies. As is seen in FIG. 1, the so-called Bragg curve of the energy loss versus penetration depth shows a pronounced peak immediately before the protons come to rest. In the art these peaks are referred to as "Bragg peaks". The penetration depth or location of the Bragg peak depends on the energy of the proton beam: The higher the energy, the larger the penetration depth. By combining a plurality of proton beams with different energies, a dose as shown by the envelope curve in FIG. 1 can be obtained, which has a maximum in a certain target region, which is below this maximum between the ion source and the target region and which drops sharply to zero behind the target region. Accordingly, using protons or other ions in radiation therapy, an adverse effect to healthy tissue in front of and behind the tumor region can be drastically reduced as compared to x-ray radiation.

While ion radiation therapy therefore has the capability of a more precise targeting of the tumor as compared to x-ray radiation therapy, the beneficial effect clearly depends on whether one is able to precisely deliver the dose to the target region as planned. This in fact remains one of the current challenges of ion radiation therapy.

Range uncertainties might become most problematic for ion beams having their Bragg peak located at the distal edge of the tumor with an organ at risk in close proximity. To compensate uncertainties caused by planning and delivery, it is clinical practice to intentionally irradiate a larger volume known as planning target volume (PTV) encompassing the tumor and additional safety margins introduced to ensure with confidence a high and confined dose level within the clinical target volume (CTV). In the advent of high precision radiation therapy not only a safer but also a more aggressive, so-called dose escalation treatment is desirable, but currently hindered by the imprecise knowledge of the Bragg peak locations.

The imprecise knowledge of the Bragg peak location is a well-known problem in the medical physics community and is studied by various groups, as for example summarized in Lomax et al.: "A treatment planning inter-comparison of proton and intensity modulated photon radiotherapy" in "Radiotherapy and Oncology", 51(3):257-271, 1999, Krimmer et al.: "Prompt-gamma monitoring in hadrontherapy: A review" in "Nuclear Instruments and Methods in Physics Research Section A: Accelerators, Spectrometers, Detectors and Associated Equipment", 878:58-73, 2018 and Parodi et al.: "In vivo range verification in particle therapy" in "*Medical Physics*", 45(11):e1036-e1050, 2018.

Besides robust treatment planning approaches as described in Unkelbach et al.: "Robust radiotherapy planning" in "*Physics in Medicine & Biology*", 63(22):22TR02, 2018, imaging techniques e.g. dual-energy CT or proton radiography/tomography are under investigation to improve pre-treatment proton range predictions, as for example described in Parodi et al.: "In vivo range verification in particle therapy" in "*Medical Physics*", 45(11):e1036-e1050, 2018 and Johnson et al.: "Review of medical radiography and tomography with proton beams." in "Reports on progress in physics", 81(1):016701, 2017.

Complementary, an in-vivo treatment verification method—ideally in real time for clinically relevant dose levels—would allow precise range adjustments, mitigating problems related to range uncertainties. As all protons stop inside the patient, current in-vivo range verification approaches typically rely on correlating the proton range to secondary emissions generated by the impinging protons.

As described in Zhu et al.: "Proton therapy verification with pet imaging" in "Theranostics", 3(10):731, 2013, positron emission tomography is based on the radioactive decay of radionuclides produced in non-elastic nuclear interactions between the tissue and the protons. The resulting activity pattern deduced from the measurement of coincident 511 keV photons resulting from the annihilation of the positron emitted in the β+-decay offers a typically retrospective evaluation of the stopping location of the protons. This technique depends on the half life times of the positron emitting radioactive isotopes which lie, depending on the isotope, between milliseconds and minutes. During this time the isotopes can be delocalized due to perfusion and other processes, which results in a so-called washout-effect thereby compromising the interpretation of the signal.

A second, more direct approach also relying on nuclear interactions is given by the detection of MeV prompt photons, as described in Krimmer et al.: "Prompt-gamma monitoring in hadrontherapy: A review" in "Nuclear Instruments and Methods in Physics Research Section A: Accelerators, Spectrometers, Detectors and Associated Equipment", 878: 58-73, 2018. Here, the excited target nuclei rapidly emit characteristic photons which are referred to as prompt gammas. The detection of prompt gammas reveals information about the ion beam range with an accuracy of one millimeter under clinical conditions in a homogeneous phantom, as is described e.g. in Hueso-Gonzdlez et al: "A full-scale clinical prototypefor proton range verification using prompt gamma-ray spectroscopy" in "*Physics in Medicine & Biology*", 63(18):185019, 2018.

A drawback for both methods, i.e. PET imaging and prompt gamma monitoring, is that the signal generation depends on the nuclear reaction threshold and is thus not predominantly generated at the Bragg peak but rather along the total beam path. In addition, the registration of the gammas is performed in the coordinate system of the detector which makes a direct mapping to the patient's anatomy error prone as potential movements of the patient have to be monitored additionally.

A third approach for in-vivo range verification is given by ionoacoustics which is based on the emission of an acoustic wave due to local energy deposition. In J. Tada et al., "Time Resolved Properties of Acoustic Pulses Generated in Water and in Soft Tissue by a Pulsed Proton Beam Irradiation—A Possibility of Dose Distribution Monitoring in Proton Radiation Therapy", Med. Phys. 18 (6), 1991, time-resolved acoustic pulses were generated in water and soft tissue by pulsed proton beam irradiation. The spatial resolution of depth dose distribution at the clinically applied beam intensity using time-of-flight measurement was estimated to be about 3 mm. In following experiments by the same research group, acoustic pulse signals have been observed even during therapy, see Y. Hayakawa et al., "Acoustic Pulse Generated in a Patient During Treatment by Pulsed Proton Radiation Beam, Radiation Oncology Investigations", 3 (1995), 42-45.

However, although this technique has been proposed some 25 years ago, it has so far not led to significant practical applications. One problem associated with the ionoacoustic measurement technique is the comparatively low signal to noise ratio, which makes precise measurements difficult.

A significant improvement in the measurement precision is described in WO 2016/009042 A1, which is due to some of the co-inventors of the present invention, and in which an intensity modulated ion beam was employed, wherein the intensity modulation comprises one or more modulation frequency components. An acoustic signal attributable to the time dependent energy deposition in said absorptive medium by said intensity modulated ion beam is detected, and at least one modulation frequency component of the acoustic signal corresponding to a respective one of the one or more modulation frequency components of said intensity modulation is extracted. Then, information regarding the location of the energy deposition is derived based on a time lag between the timing of the intensity modulation of said ion beam and said acoustic signal.

Unlike the method of Tada et al. and Hayakawa et al., the technique of WO 2016/009042 A1 is not focused all on individual independent pulses and time-of-flight measurements, but on "frequency information", which was found to significantly improve the measurement precision as compared to methods based on individual pulses and simple time-of-flight measurements. One advantage highlighted in this application is that since the acoustic signals will exhibit the same frequency as the intensity modulation of the ion beam, this frequency information can be used for filtering out the signals from the background, for example by using a narrowband filter or a lock-in amplifier, thereby ameliorating the effects of the typically poor signal-to-noise ratio (SNR). It is shown that this way, the acoustic signals, which typically will be comparatively weak, can be better distinguished from the background.

Nevertheless, in spite of these improvements, a precise determination of the location of energy deposition by the ionoacoustic methods remains challenging.

SUMMARY OF THE INVENTION

The problem underlying the invention is to provide a method and an apparatus for determining information regarding the location of energy deposition of an ion beam, such as a proton beam, in an absorptive medium, such as the tissue of a patient undergoing radiation therapy, with improved precision and/or reduced dose deposition.

According to one aspect of the invention, a method of determining information regarding the location of energy deposition of an ion beam, in particular a proton beam, in an absorptive medium, in particular in the tissue of a patient undergoing radiation therapy, is provided. The method comprises the following steps:

generating a pulsed ion beam, detecting a time-resolved acoustic signal, said time-resolved acoustic signal comprising an energy-deposition-signal component attributable to the energy deposition of an individual pulse of said pulsed ion beam in said absorptive medium, determining relative timing information of the energy deposition of said individual pulse with respect to said time-resolved acoustic signal, providing a matched filter for processing the time-resolved acoustic signal, said matched filter being configured to facilitate detecting said energy-deposition-signal component within said time-resolved acoustic signal, applying said matched filter to said time-resolved acoustic signal to thereby obtain a filtered time-resolved signal, deriving, from said filtered time-resolved signal, occurrence timing information related to the occurrence of said energy-deposition signal component in said time-resolved acoustic signal, and deriving information regarding the location of the energy deposition based, at least in part, on a delay between said energy deposition of said individual pulse and said occurrence timing information.

Contrary to the frequency-based technique described in WO 2016/009042 A1, in which a modulated ion beam was used and a corresponding modulation in the detected time-resolved acoustic signal was filtered via the known modulation frequency, the method of the invention again uses a purely time-based technique, in which the location of energy deposition is derived from individual pulses, rather than from modulated beams or "pulse trains" that according to WO 2016/009042 A1 are analyzed as a whole.

Indeed, it was inter alia the poor SNR associated with the time-resolved ionoacoustic signals that incited some of the present co-inventors to focus on a frequency-based approach as set forth in WO 2016/009042 A1, in which the noisy signal could be filtered based on the frequency information, and in which significant improvement indeed was made.

However, the inventors noticed that surprisingly, determining the location of energy deposition based on the ionoacoustic signal associated with individual ion beam pulses can be dramatically improved if the time-resolved acoustic signal is processed with a matched filter. As the skilled person will appreciate, the typical application of a matched filter is to detect the presence of a known signal using a "template" that contains characteristic information of the signal, typically including signal generation and transport as well as detection characteristics. In some embodiments, the expected signal itself can form such template. This approach is for example widely used in digital communications, where one knows that the signal is of binary structure, for example in a non-return-to-zero (NRZ) line code, and where the template could be a (NRZ) pulse used to encode digital "1" in the digital signal (i.e. the "known signal" to look for).

The skilled person will hence appreciate that the matched filter technique is a filtering technique that is commonly applied in situations where there is a "known signal" contained in an unknown signal. However, the matched filtering is not an obvious technique to apply for ionoacoustic signals, where there is no "known signal" to begin with.

Using extensive computer simulations and a convolution of the results with beam characteristics as well as sensor transfer functions, the inventors however developed an understanding of how the signal of interest included in a noisy background could look like, and how the interesting signal component could be derived in practical applications. The signal component of interest is referred to as the "energy-deposition-signal component" herein. It is contained within the total time-resolved acoustic signal and is the signal component that is attributable to the energy deposition of an individual pulse of said pulsed ion beam in the absorptive medium. Moreover, the inventors could confirm that with the thus developed prediction of the energy-deposition-signal component, a matched filter could be provided that allows for dramatically increasing the SNR.

According to the invention, the thus provided matched filter is applied to the time-resolved acoustic signal to thereby obtain a filtered time-resolved signal. From this filtered time-resolved signal, occurrence timing information related to the occurrence of the energy-deposition-signal component in said time-resolved acoustic signal is derived.

For example, if the energy-deposition-signal component comprises a unique pronounced peak, then the "occurrence" of the energy-deposition-signal component in the time-resolved acoustic signal could simply amount to the occurrence of this peak within the time-resolved acoustic signal, and the "occurrence timing information" would then be the point in time at which this single peak is located within the time-resolved acoustic signal. However, the waveform of the energy-deposition-signal component may be more complex, and the occurrence timing information could be likewise more complex than the timing of a single peak, but could for example represent timing information associated with one or more complex features of the energy deposition signal component waveform.

Irrespectively of how the "occurrence timing information" is defined in respective embodiments of the invention, it generally corresponds to timing information that represents an arrival time of the energy-deposition-signal component within the time-resolved acoustic signal. Moreover, in view of the relative timing information of the energy deposition of the individual pulse with respect to the time-resolved acoustic signal, a delay between the energy deposition of the individual pulse and the occurrence timing information can be derived, which depends on the distance travelled by the time-resolved acoustic signal between the location of energy deposition and the location of its detection. Accordingly, from this delay, information regarding the location of the energy deposition can be derived.

In a preferred embodiment, said step of providing the matched filter comprises providing a template, said template representing a predicted waveform of the energy-deposition-signal component.

In a preferred embodiment, applying said matched filter to said time-resolved acoustic signal comprises correlating said template with said time-resolved acoustic signal, or convolving the time-resolved acoustic signal with a conjugated time-reversed version of the template. The details of this operation will be explained in more detail with reference to specific embodiments below.

In preferred embodiments, the step of providing said template comprises determining the template at least in part by computer simulation. Herein, said simulation may comprise simulating the template as an ionoacoustic signal caused by an estimated time-dependent energy deposition distribution of the ion beam in said absorptive medium. Herein, the estimated time-dependent energy deposition may be obtained at least in part by computer simulation as well, as will be illustrated in more detail with reference to specific embodiments below.

In preferred embodiments, said simulation of said template as an ionoacoustic signal is based on space-resolved information about mass density and/or speed of sound in said absorptive medium. With this space-resolved information, the propagation of the ionoacoustic signal through the absorptive medium can be simulated more realistically, and the waveform of the energy-deposition-signal component can be predicted with more precision. In particularly useful applications, said absorptive medium is tissue of a patient, and the space-resolved information is obtained from medical images obtained during one or both of a treatment planning and during the radiation therapy. In a related embodiment, said medical images are ultrasound images, magnetic resonance tomography (MRT) images, x-ray images, CT images, or combinations thereof. From these medical images, information regarding the mass density and/or speed of sound can be discerned. For example, in such medical images, and in particular in combinations of medical images, different types of tissue, fat, water, bone and the like can be identified, for which mass density and said speed of sound are at least approximately known. In addition, in ultrasound images, these properties can be also be derived from analyzing the propagation of sound waves through the tissue.

In a particularly advantageous embodiment, said step of providing said template further comprises accounting for transducer characteristics of a transducer used for detecting the time-resolved acoustic signal. This way, the efficiency of the matched filter can further be improved. In preferred embodiments, the transducer characteristics are accounted for using a transfer function that is associated with said transducer. Such transfer functions can be obtained by specifications provided by the manufacturer or measured in a phantom under similar conditions as in the real applications. The transducer transfer function can also be approximated by a bandpass filter like a Butterworth bandpass filter or similar or by a numerical representation of experimentally generated transducer transfer functions.

In preferred embodiments, said template is subjected to a self-adapting and/or self-optimizing procedure, in order to more realistically represent the energy-deposition-signal component at the detection apparatus. For example, a preliminary template can be generated by computer simulation, and subsequently improved such as to lead to improved filtering. For example, said self-adapting and/or self-optimizing procedure preferably comprises varying the time length of the template such as to maximize the SNR. Generally, a longer template exhibiting more features carries more information, but possibly less pronounced information. For example, the energy-deposition-signal component could include various secondary peaks due to reflection of part of the ionoacoustic wave at bony structures, or at other interfaces within the body where the elastic properties change, that may be delayed with respect to a main peak thereof. These types of features can be assessed by computer simulation using the techniques described in more detail below, for example when taking the above-mentioned space-resolved information about mass density and/or speed of sound in said absorptive medium into account, and can hence be included in the template. However, these more detailed features can be rather small, so that it cannot be easily predicted whether accounting for these additional, delayed features in the template actually improves the filter, or whether better results can be obtained by using a shorter template restricted to the main, most pronounced features. Herein, "using a shorter template" may simply mean that a longer template that has been previously prepared is truncated, or in other words, that only a portion thereof is used in applying the matched filter.

It is also possible to obtain a template adapted to an experiment on a phantom that has a similar arrangement of materials as in the patient. The template could be measured for the ionoacoustic signal under the same irradiation conditions as in the patient but at much higher doses. This would give the signal at a much better/higher SNR and allows to directly extract an experimental template and co-register it in an ultrasound image of the phantom. Range uncertainties could be independently measured by dose monitors in the phantom to get approved information on extracting ranges from the filtered signal.

In a preferred embodiment, said step of providing said template comprises optimizing the template in an iterative procedure, to thereby increase the SNR. Herein, the optimization can again involve choosing an optimum time length of the template, i.e. a time length that leads to the largest SNR. In some embodiments, analysis results of a plurality of signals from varying irradiation geometries obtained for phantoms and for patients can be compiled, and based on this "expert knowledge", more robust predictions of templates can be made for various measurement conditions. This prediction can for example be made using machine learning or based on artificial intelligence.

In a preferred embodiment, providing said template comprises selecting one or more templates from a database of previously generated templates. Herein, said previously generated templates may comprise templates which are, at least in part, based on energy-deposition-signal components obtained by experiment using doses higher than 40 Gy, preferably higher than 100 Gy. Generally, the SNR of the time-resolved acoustic signal is increased when more energy is deposited However, in clinical applications, the energy deposition can of course not be arbitrarily increased, because there is a limit of the suitable dose to be received by the patient. However, it is possible to empirically determine energy-deposition-signal components on nonliving samples, where the dose restrictions do not apply, and to store the same as templates in a database.

In a related embodiment, said one or more selected templates are further modified to account for one or both of the shape of the individual ion pulse and the sensor characteristics of a sensor used for detecting the time-resolved acoustic signal, and/or heterogeneities in the beam and in the acoustic path. That is to say, knowing how the actually used ion pulse differs from the ion pulse that was used for generating the previously generated templates in the database, the template can be modified such as to better match the present situation. The same is true for the characteristics of the sensor that is used for detecting the time-resolved acoustic signal, such as the aforementioned transducer. The influence of the present sensor characteristics on the measured time-resolved acoustic signal can be accounted for by modifying the selected template accordingly, for example by applying a suitable filter to the selected template.

In preferred embodiments, said relative timing information of the energy deposition of said individual pulse with respect to said time-resolved acoustic signal is determined based on a trigger signal indicating the arrival of a pulse of said pulsed ion beam in the absorptive medium.

Herein, said trigger signal may be one of
  an electric signal provided by electronic components involved with generating said pulsed ion beam, in particular provided by electronic components of a chopper,
  a signal provided by a detector provided in front of the absorptive medium, and
  a signal provided by a detector for detecting secondary radiation due to the interaction of the ion beam with the absorptive medium.

In some embodiments, said information regarding the location of energy deposition is an information about the position along the axis of the ion beam where the energy deposition per unit volume is maximum. This information, which can be graphically referred to as the "range" of the ion beam, is in many respects the most important information concerning the location of energy deposition, since it is the information that cannot be easily predicted by other means. On the other hand, the direction of the beam axis and the beam profile in the plane perpendicular to the beam axis, which are of course as important regarding the proper treatment, can be determined and controlled by other means.

However, in other embodiments, the aforementioned information regarding the location of energy deposition may correspond to or be a one-, two- or three-dimensional energy dose distribution.

In a preferred embodiment, said time-resolved acoustic signal is detected using at least one detection apparatus, wherein said detection apparatus is located within a cone having
  its apex at the position along the ion beam axis where the energy deposition per unit volume is maximum,
  a rotation axis coinciding with an axis of said ion beam, and
  an aperture angle of 450 or less, preferably of 250 or less and most preferably of 120 or less,
and is in particular located on the ion beam axis. If the detection apparatus is located on or close to the beam axis, the position along the ion beam axis where the energy deposition per volume is maximum can be easily and precisely determined based on the aforementioned delay between said energy deposition of said individual pulse and said occurrence timing information.

In a preferred embodiment, said time-resolved acoustic signal is detected using at least one detection apparatus, wherein said at least one detection apparatus comprises a ionoacoustic transducer for detecting said time-resolved acoustic signal, and wherein said ionoacoustic transducer is adapted to record ultrasonic images of said absorptive medium as well. This way, the ionoacoustic signal travels through the same absorptive medium (tissue) that can be imaged using ultrasound imaging. This allows for detecting the acoustic properties of the absorptive medium through which the ionoacoustic signal travels, which can be used for generating or adapting templates. Moreover, determining the travelled distance from the location of energy deposition in "real" 3D space, such as with respect to the coordinate system of the radiation therapy room, from the delay between said energy deposition of said individual pulse and said occurrence timing information requires a precise knowledge of the speed of sound of the tissue through which the ionoacoustic signal propagates. Unfortunately, this speed of sound varies throughout the tissue, and may not be precisely known. The space-dependent speed of sound can however be assessed at least approximately from the ultrasound image to thereby improve the precision of the determined distance between the energy deposition and the ionoacoustic transducer in real 3D space. Moreover, since the ultrasound signals are affected by the same local variations in speed of sound of the tissue as the ionoacoustic signals, it becomes possible to associate this distance with a distance in the ultrasound image without having to account for the variations in the speed of sound. In other words, it is possible to locate the location of energy deposition very precisely in the coordinate system of the ultrasound image rather than in "real 3D space", which in many cases is all the clinically relevant information one needs.

As will be shown below with reference to specific embodiments, the main frequencies of the ionoacoustic signal are typically lower than those used in ultrasound transducers. Accordingly, it may not always be practical or preferred to use the same transducer for ultrasound imaging and ionoacoustic detection. Accordingly, in alternative embodiments, an ultrasound transducer is provided in a known spatial relationship to said ionoacoustic transducer, allowing to correlate the time-resolved acoustic signal detected by the ionoacoustic transducer with the ultrasound images obtained by the ultrasound transducer. Herein, the ultrasound transducer is preferably provided close to, and most preferably directly adjacent to the ionoacoustic transducer, which means that the ionoacoustic signals that are detected by the ionoacoustic transducer propagate through essentially the same tissue as at least some of the ultrasound signals. For example, the ionoacoustic transducer and the ultrasound transducer may be located so close to each other that two lines connecting a presumed location of energy deposition with the center of the ionoacoustic transducer and with the center of the ultrasound transducer, respectively, form an angle that is less than 30°, preferably less than 10°.

In preferred embodiments, said location of the energy deposition is derived with respect to a coordinate system associated with an ultrasound image recorded with said ionoacoustic transducer or with said ultrasound transducer in said known spatial relationship to said ionoacoustic transducer. As mentioned before, since the ultrasound image experiences essentially the same local variations in speed of sound as the ionoacoustic signal, it is possible to determine the location of energy deposition very precisely with respect to the ultrasound image. For example, the location of energy deposition can be indicated in a visual presentation of the ultrasound image, and it can be readily checked whether it is in agreement with the intended treatment.

In related embodiments, the method may therefore further comprise a step of providing a medical image in which said location of energy deposition is indicated, wherein said medical image is said ultrasound image, an image derived from said ultrasound image, or a medical image acquired with an imaging modality different from ultrasound imaging that is co-registered with said ultrasound image.

In a related embodiment, a target area for energy deposition according to a treatment plan is associated with said medical image, wherein said method further comprises a step of determining whether the location of energy deposition with regard to said target area deviates from said treatment plan, and in case the deviation exceeds a predetermined threshold, deriving control or operating parameters such as to decrease the deviation. Herein, the control or operating parameters may relate to the energy of the ion beam, where larger energies lead to a shift of the Bragg peak deeper into the tissue, or to positioning parameters for a treatment table on which a patient is placed.

In a preferred embodiment, deriving said location of energy deposition with respect to the coordinate system associated with said ultrasound image is based on said delay between said energy deposition of said individual pulse and said occurrence timing information, wherein said delay is corrected by a predetermined time offset. This predetermined offset does not reflect the "time-of-flight" of the ionoacoustic signal, but rather internal properties of the detection apparatus, delays associated with the measurement electronics and the like. The inventors noticed that with the submillimeter precision obtainable with the method of the invention, these delays actually become relevant.

In a related embodiment, the method further comprises a step of determining said time offset by carrying out a calibration measurement using the same detection apparatus on a phantom in which a source of an acoustic signal is provided that is discernible in the ultrasound image. Then, it becomes possible to adjust the time offset such that the predicted localization of the source of acoustic signal within the ultrasound image as derived from the delay between said energy deposition of said individual pulse and said occurrence timing information matches the position where the source of acoustic signal is discerned in the ultrasound image. For this purpose, an optoacoustic setup may be employed, in which a pulsed laser induces an acoustic signal in a thin absorber. Such acoustic signal is close to a delta pulse. In experiments carried out by the inventors, the absorber was formed by a blacked aluminum foil, which allowed for generating very strong and short optoacoustic pulses.

In a preferred embodiment, said detection apparatus for detecting said time-resolved acoustic signal comprises a piezo-electric element, in particular a PZT or a PVDF element. In addition or alternatively, the detection apparatus may further comprise a detector for detecting γ-radiation, in particular a scintillation detector or a solid state γ-radiation detector for generating the aforementioned trigger signal.

In a preferred embodiment, said at least one detection apparatus is configured for insertion into a hollow organ, in particular into the gastro-intestinal tract, into the trachea or lung, into the colon, into the rectum, into a blood vessel, into the urethra or into the bladder.

The inventors have noticed that the SNR in the filtered time-resolved signal can be increased if the pulse duration $t_d$ is suitably chosen. The proper choice of pulse duration $t_d$ depends on the energy of the ions used, in particular the spread in range of the ion beam. The inventors have systematically determined optimum pulse durations for proton pulses for clinically relevant energies in a range of 20 MeV to 260 MeV, such that the SNR of the filtered time resolved signal, i.e. after applying the matched filter, is the highest. Accordingly, in a preferred embodiment, the ions are protons, and the pulse duration $t_d$ is chosen as a function of the proton energy $E_P$, such that $$f(E_P) \leq t_d \leq g(E_P),$$

wherein $t_d$ is measured in μs, $E_P$ is measured in MeV and chosen from a range between 20 MeV and 260 MeV, and $f(E_P)$, $g(E_P)$ are second order polynomials defined as $$f(E_P) = p1(E_p)^2 + p2\, E_P + p3 \text{ and}$$

$$g(E_P) = q1(E_P)^2 + q2\, E_P + q3, \text{ respectively,}$$

wherein the coefficients $p_i$ and $q_i$ with $i=1\ldots 3$ are chosen as follows:

$p1=1.476*10^{-5}$, $p2=0.002486$, $p3=-0.05185$, and
$q1=0.000118$, $q2=0.03548$, $q3=-0.9488$,
preferably
$p1=2.371*10^{-5}$, $p2=0.003549$, $p3=-0.1074$, and
$q1=0.0001096$ $q2=0.01909$ $q3=-0.4322$
and most preferably
$p1=3.731*10^{-5}$ $p2=0.004948$ $P3=-0.1487$, and
$q1=8.8*10^{-5}$ $q2=0.01039$ $q3=-0.2162$.

Herein, the pulse duration $t_d$ is given as the full width at half maximum (FWHM) of a Gaussian fitted in a least square fit to the actual pulse shape. Note that this is not meant to imply that the pulse shape must necessarily be similar to a Gaussian shape, instead, irrespectively of the exact pulse shape, the pulse duration $t_d$ is to be determined in this manner. This may in particular be applied to pulses that are more similar to a rectangular pulse than to a Gaussian pulse.

In a related embodiment, for a given dose limit of protons of a given proton energy $E_P$ to be irradiated into tissue of a patient, the dose is split into two or more pulses, each of which, or at least the predominant part of which have a pulse duration $t_d$ chosen from the preferred range recited above. The inventors noticed that for achieving high SNR of the filtered signal, it is advantageous to apply the dose split up in several individual pulses of the same proton energy and with advantageous pulse durations $t_d$ according to one of the ranges defined above, rather than applying the entire dose in a single pulse of longer duration. Depending on the given dose limit, it may not be possible to split the dose limit into individual pulses all of which having a pulse length according to the above preferred ranges, but it is sufficient if at least the predominant part of the pulses are chosen accordingly.

In a preferred embodiment, the ion beam is a proton beam, and the mean beam current within the proton pulse is at least 5 nA, preferably at least 50 nA and most preferably at least 500 nA for dose deliveries of more than 10 Gy, and at least 50 nA, preferably at least 500 nA and most preferably at least 5 µA for dose deliveries of more than 1 Gy. The inventors could confirm that for the improved SNR of the ionoacoustic signal, it is indeed advantageous to choose the beam current as high as possible, and to adapt the pulse length accordingly such as to obtain a desired dose. This is even true if this means that the pulse lengths are shortened to fall below the preferred pulse duration intervals defined above. On the other hand, if the pulse length thus chosen should still exceed the above ideal pulse length, it is again preferred to split the pulse up into two or more pulses at or close to the ideal pulse length. In order to meet other preferences of the treatment system relying on lower mean beam currents than being ideal for ionoacoustic detection, time intervals between single pulses can be arbitrarily chosen to reduce mean beam current to the required level.

A further aspect of the invention relates to an apparatus for determining information regarding the location of energy deposition of a pulsed ion beam, in particular a pulsed proton beam, in an absorptive medium, in particular in the tissue of a patient undergoing radiation therapy, said apparatus comprising:

a detection apparatus for detecting a time-resolved acoustic signal, said time-resolved acoustic signal comprising an energy-deposition-signal component attributable to the energy deposition of an individual pulse of said pulsed ion beam in said absorptive medium, a device for determining relative timing information of the energy deposition of said individual pulse with respect to said time-resolved acoustic signal, and a control system, said control system configured for applying a matched filter to said time-resolved acoustic signal to thereby obtain a filtered time-resolved signal, said matched filter being configured to facilitate detecting said energy-deposition-signal component within said time-resolved acoustic signal, deriving, from said filtered time-resolved signal, occurrence timing information related to the occurrence of said energy-deposition signal component in said time-resolved acoustic signal, and deriving information regarding the location of the energy deposition based, at least in part, on a delay between said energy deposition of said individual pulse and said occurrence timing information.

In a preferred embodiment, said matched filter is based on a template, said template representing a predicted waveform of the energy-deposition-signal component.

In a preferred embodiment, said detection apparatus comprises a transducer for detecting the time-resolved acoustic signal, and the template is adapted to account for the characteristics of said transducer.

In a preferred embodiment, said control system is further configured to subject said template to a self-adapting and/or self-optimizing procedure, wherein said self-adapting and/or self-optimizing procedure preferably comprises varying the time length of the template.

In a preferred embodiment, said control system is configured for optimizing the template in an iterative procedure, to thereby increase the SNR.

In a preferred embodiment, said control system is configured for selecting one or more templates from a database of previously generated templates.

Said control system is preferably configured for modifying said one or more selected templates to account for one or both of the shape of the individual ion pulse and the characteristics of a sensor used for detecting the time-resolved acoustic signal and/or heterogeneities in the beam and in the acoustic path.

In a preferred embodiment, said device for determining relative timing information of the energy deposition of said individual pulse with respect to said time-resolved acoustic signal utilizes a trigger signal indicating the arrival of a pulse of said pulsed ion beam in the absorptive medium, wherein said trigger signal is one of an electric signal provided by electronic components involved with generating said pulsed ion beam, in particular provided by electronic components of a chopper, a signal provided by a detector provided in front of the absorptive medium, and a signal provided by a detector for detecting secondary radiation due to the interaction of the ion beam with the absorptive medium.

In a preferred embodiment, said at least one detection apparatus comprises an ionoacoustic transducer for detecting said time-resolved acoustic signal, wherein said ionoacoustic transducer is adapted to record ultrasonic images of said absorptive medium as well, or wherein said apparatus further comprises an ultrasound transducer in a defined spatial relationship to said ionoacoustic transducer, wherein said ultrasound transducer is preferably arranged close to, and most preferably directly adjacent to the ionoacoustic transducer.

In a preferred embodiment of said apparatus said control system is configured to derive said location of the energy deposition with respect to a coordinate system associated with an ultrasound image recorded with said ionoacoustic transducer or with said ultrasound transducer in said defined spatial relationship to said ionoacoustic transducer.

In a preferred embodiment of said apparatus, said control system is further configured for providing a medical image in which said location of energy deposition is indicated, wherein said medical image is one of said ultrasound image, an image derived from said ultrasound image, and a medical image acquired with an imaging modality different from ultrasound imaging that is co-registered with said ultrasound image.

In a preferred embodiment of said apparatus, said control system is configured for determining whether the location of energy deposition with regard to a target area associated with said medical image deviates from a treatment plan, and is further configured for deriving control or operating parameters such as to decrease the deviation in case the deviation exceeds a predetermined threshold, wherein the control or operating parameters preferably relate to the energy of the ion beam or to positioning parameters for a treatment table on which a patient is placed.

In a preferred embodiment of said apparatus, said time-resolved acoustic signal is detected using at least one detection apparatus, wherein said at least one detection apparatus comprises a piezo-electric element, in particular a PZT or a PVDF element, and/or wherein said detection apparatus further comprises a detector for detecting γ-radiation, in particular a scintillation detector or a solid state γ-radiation detector.

Preferably, said detection apparatus is configured for insertion into a hollow organ, in particular into the gastro-intestinal tract, into the trachea or lung, into the colon, into the rectum, into a blood vessel, into the urethra or into the bladder.

In a particularly preferable embodiment of the apparatus, the ions are protons, and said control system is configured to control the pulse duration $t_d$ as a function of the proton energy $E_P$, such that $$f(E_P) \leq t_d \leq g(E_P),$$

wherein $t_d$ is measured in µs, $E_P$ is measured in MeV and chosen from a range between 20 MeV and 260 MeV, and $f(E_P)$, $g(E_P)$ are second order polynomials defined as $$f(E_P) = p_i(E_P)^2 + p2\, E_P + p3 \text{ and}$$

$$g(E_P) = q1(E_P)^2 + q2\, E_P + q3, \text{ respectively,}$$

wherein the coefficients $p_i$ and $q_i$ with i=1 . . . 3 are chosen as follows:
P1=1.476*10$^{-5}$, p2=0.002486, p3=−0.05185, and
q1=0.000118, q2=0.03548, q3=−0.9488,
preferably
P1=2.371*10$^{-5}$, p2=0.003549, p3=−0.1074, and
q1=0.0001096 q2=0.01909 q3=−0.4322
and most preferably
P1=3.731*10$^{-5}$ p2=0.004948 p3=−0.1487, and
q1=8.8*10$^{-5}$ q2=0.01039 q3=−0.2162.

Herein, the pulse duration $t_d$ is given as the FWHM of a Gaussian fitted in a least square fit to the actual pulse shape.

In a preferred embodiment of the apparatus, for a given dose limit of protons of a given proton energy $E_P$ to be irradiated into tissue of a patient, the control system is configured to determine respective pulse durations $t_d$ of two or more pulses to which the dose limit is distributed such that each, or at least the predominant part of these two or more pulses have a pulse duration $t_d$ chosen according to one of the preferred ranges defined above.

A yet further aspect of the invention relates to a proton beam irradiation system, comprising a source for generating a pulsed proton beam as well as an apparatus according to one of the embodiments recited above, wherein a proton beam current provided by said source for generating a pulsed proton beam is at least 5 nA, preferably at least 50 nA and most preferably at least 500 nA for dose deliveries of more than 10 Gy, and at least 50 nA, preferably at least 500 nA and most preferably at least 5 µA for dose deliveries of more than 1 Gy.

SHORT DESCRIPTION OF THE FIGURES

Figure 15:
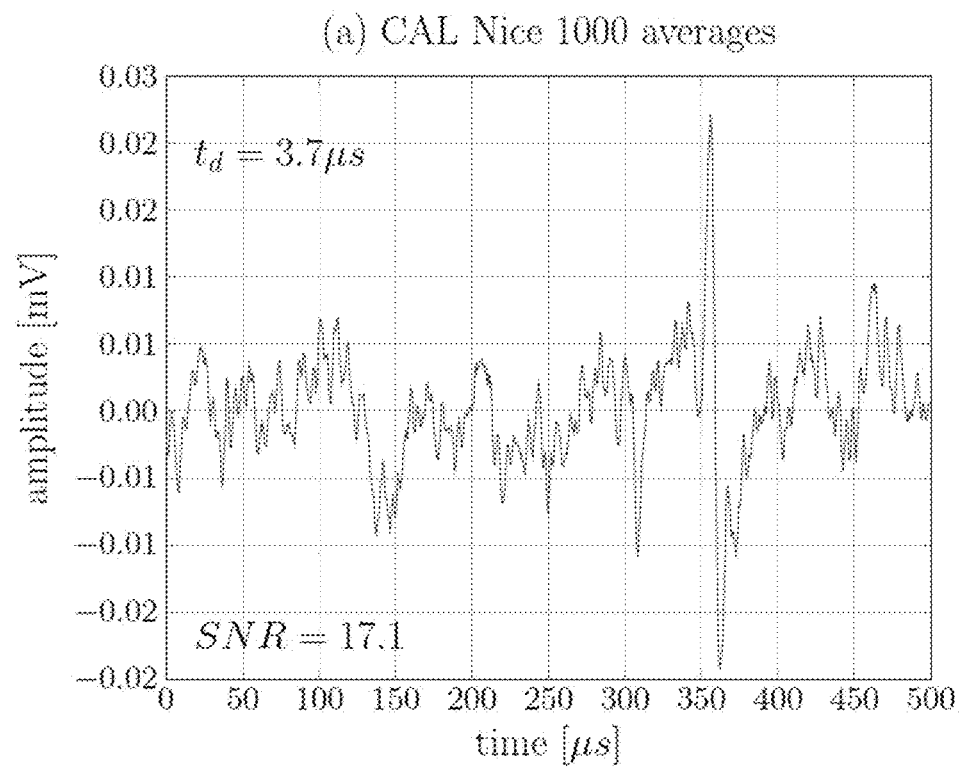

FIG. 15 shows the average of 1,000 unfiltered time-resolved acoustic signals from 220 MeV proton bunches of about 5 µs length in a water phantom. [data from Sebastian Lehrack, Walter Assmann, Damien Bertrand, Sebastien Henrotin, Joel Herault, Vincent Heymans, Francois Vander Stappen, Peter G Thirolf, Marie Vidal, Jarno Van de Walle, et al. Submillimeter ionoacoustic range determination for protons in water at a clinical synchrocyclotron. *Physics in Medicine & Biology*, 62(17):L20, 2017].

Figure 16:
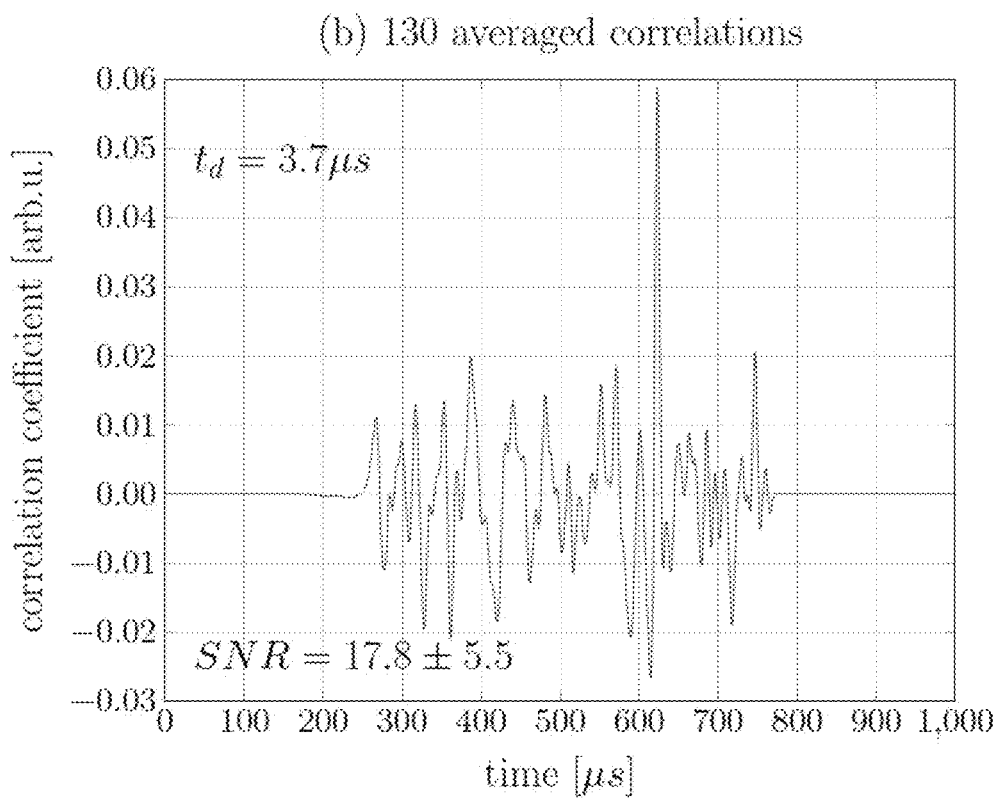

FIG. 16 shows the average of 130 filtered time-resolved signals from 220 MeV proton bunches of about 4 μs length in a water phantom. [data from Sebastian Lehrack, Walter Assmann, Damien Bertrand, Sebastien Henrotin, Joel Herault, Vincent Heymans, Francois Vander Stappen, Peter G Thirolf, Marie Vidal, Jarno Van de Walle, et al. Submillimeter ionoacoustic range determination for protons in water at a clinical synchrocyclotron. *Physics in Medicine & Biology*, 62(17):L20, 2017.]

Figure 17:
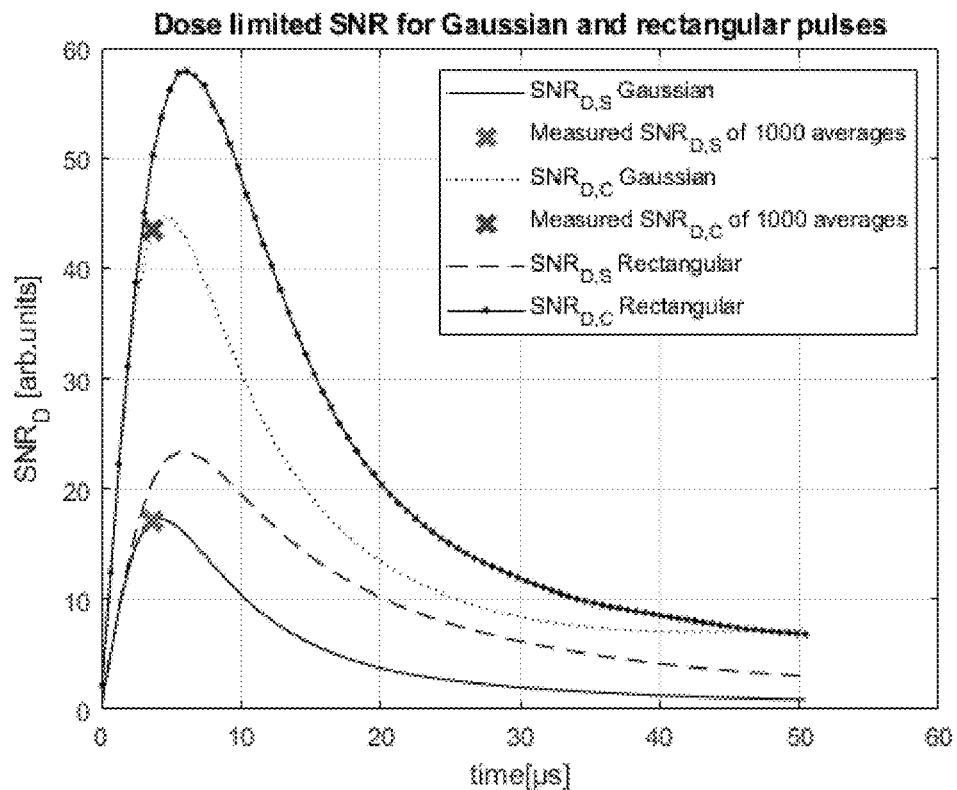

FIG. 17 shows the dose limited SNR as a function of pulse duration for Gaussian and rectangular pulses.

Figure 18:
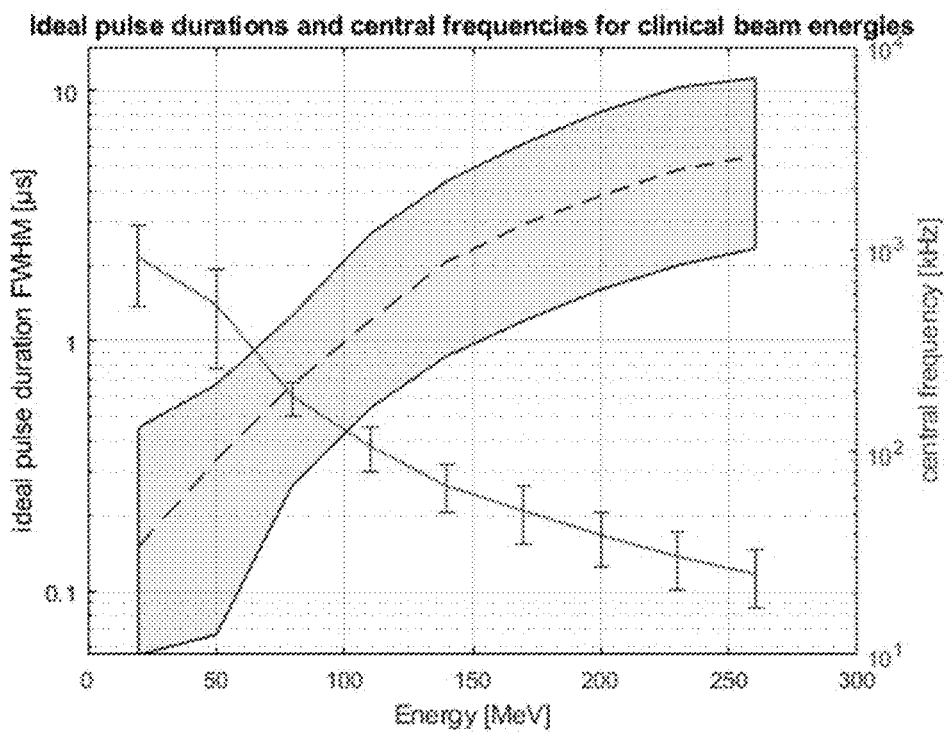

FIG. 18 shows a corridor of preferable pulsed orations considering Gaussian pulse shapes and a correlation-based evaluation for all proton energies between 20 MeV and 260 MeV.

Figure 19:
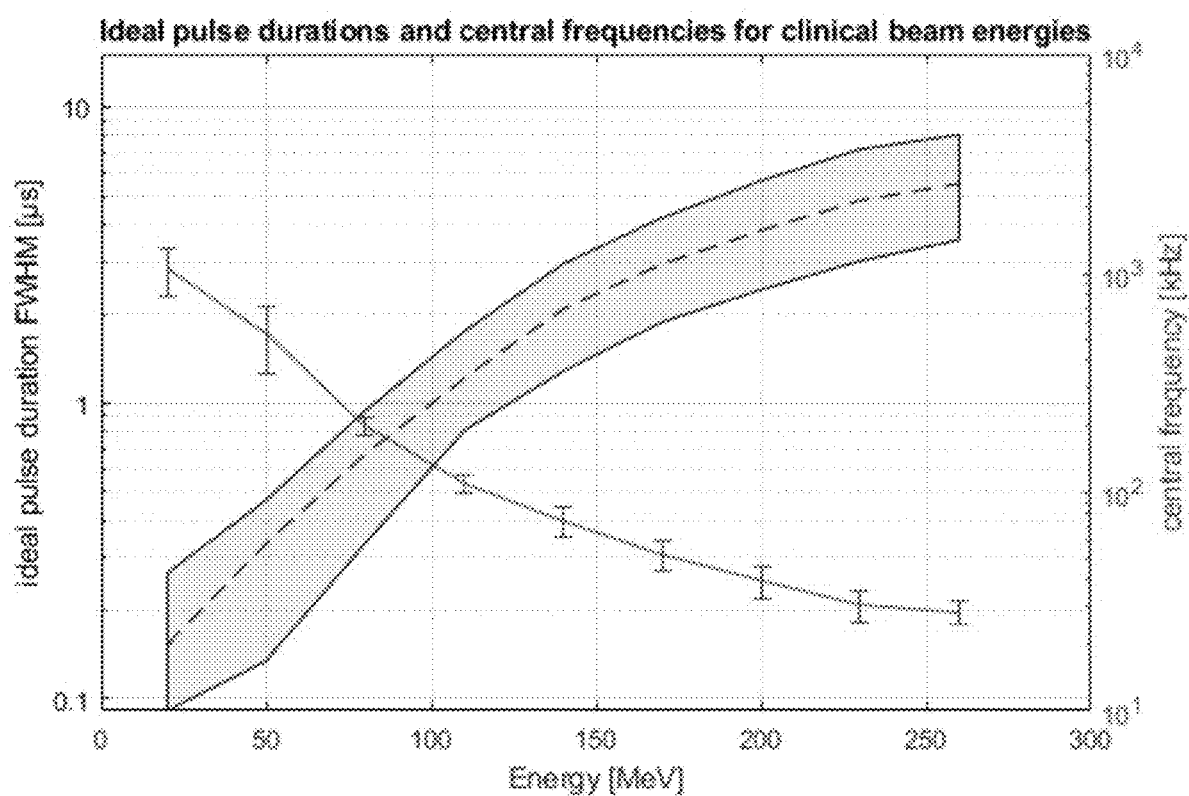

FIG. 19 shows a narrower corridor of optimal pulse durations than FIG. 18.

DESCRIPTION OF THE PREFERRED EMBODIMENTS

It is to be understood that both the foregoing general description and the following description are exemplary and explanatory only and are not restrictive of the methods and apparatuses described herein. In this application, the use of the singular may include the plural unless specifically state otherwise. Also, the use of "or" means "and/or" where applicable or unless stated otherwise. Those of ordinary skill in the art will realize that the following description is illustrative only and is not intended to be in any way limiting. Other embodiments will readily suggest themselves to such skilled persons having the benefit of this disclosure. Reference will now be made in detail to various implementations of the example embodiments as illustrated in the accompanying drawings.

Figure 1:
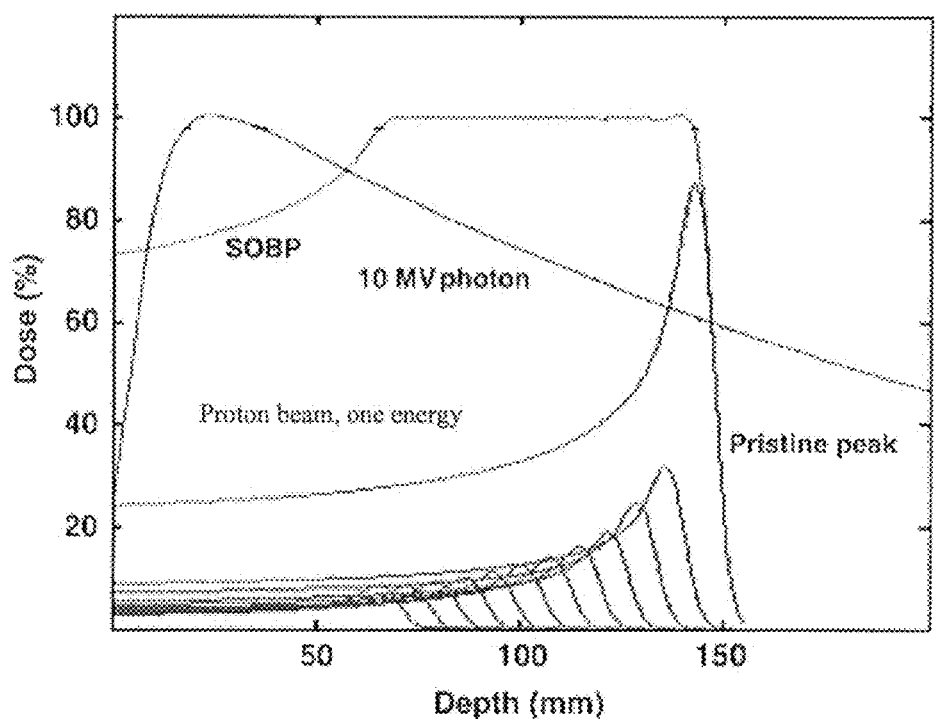
FIG. 1 is a diagram showing the energy deposition of a dose of 10 MeV photons as a function of penetration depth compared with the energy deposition of several proton beams of different energies.
Figure 2:
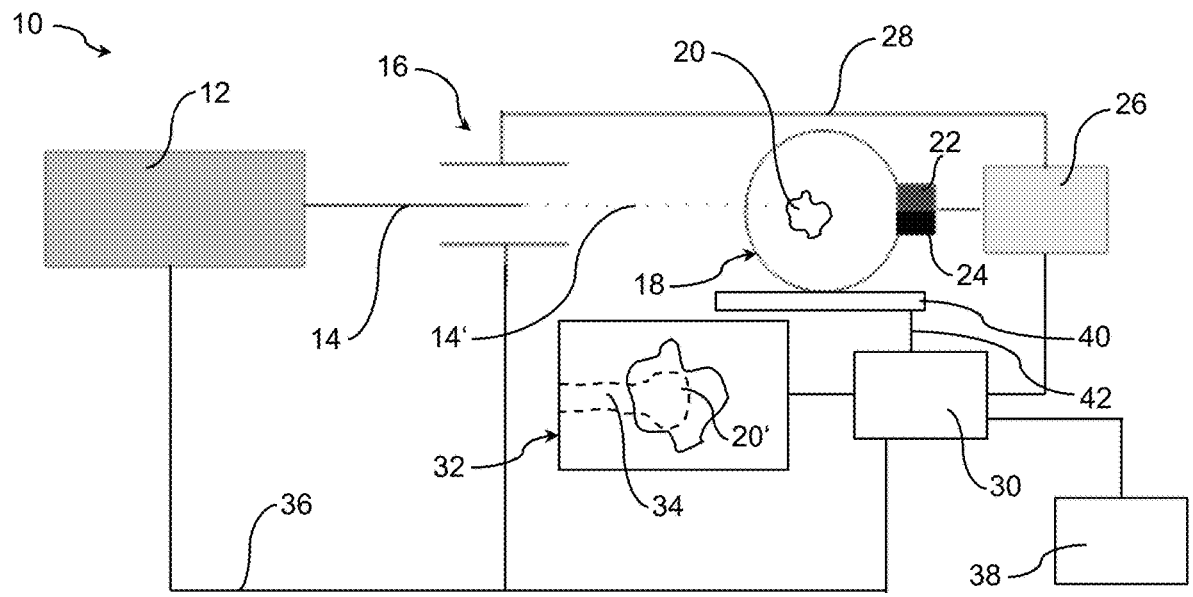
FIG. 2 is a schematic representation of a system for ion beam therapy.

FIG. 2 schematically shows a system 10 for ion beam therapy. The system 10 comprises an ion accelerator 12 for accelerating ions, such as protons, and outputting an ion beam 14. The ion accelerator 12 may for example be a linear accelerator, a cyclotron, synchro-cyclotron or a synchrotron. The ion beam 14 emitted by the ion accelerator 12 is choppped by a pulsed ion source or a chopper 16 in front, within or behind the accelerator which chops parts of the ion beam 14 and thereby generates a pulsed ion beam 14'.

Figure 3:
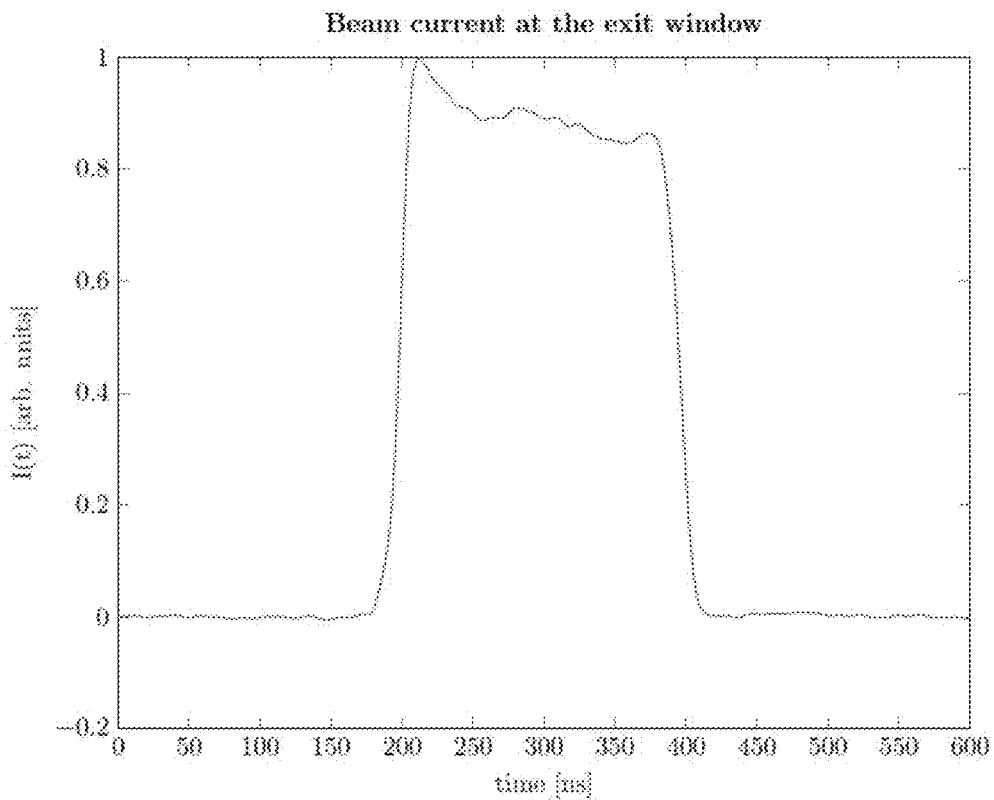
FIG. 3 shows the time profile of a proton pulse having an energy of 20 MeV, as it was used for evaluation of iono-acoustic signals as presented in FIGS. 4, 7 and 8.

FIG. 3 shows the time profile of an ion pulse, in this case a proton pulse having an energy of 20 MeV, that was obtained by a chopper like chopper 16 in experiments conducted by the inventors. As is seen in FIG. 3, the chopper allows for obtaining a close to rectangular proton pulse of controllable width. The proton pulse time profile was recorded in a separate experiment with a fast silicon detector at the beam exit window. The measurement shows that the rise time (from 10% to 90%) is roughly 15 ns which is short compared to the duration of the pulse (FWHM=193 ns). The plateau region of the beam current shows minor fluctuations which are small compared to the absolute amplitude and thus validating the approximation of a rectangular pulse shape.

The pulsed ion beam 14' is irradiated into a patient 18 suffering from a tumor 20 that is to be treated by ion radiation. The energy of the pulsed ion radiation is deposited in the tissue of the patient 18, thereby leading to a local heating, which in turn causes a "shock wave", i.e. an acoustic signal that is referred to as an "ionoacoustic signal" herein. An ultrasound transducer 22 is provided for generating ultrasound images of the patient 18, including the area where the tumor 20 resides. In a fixed spatial relation to the ultrasound transducer 22, an ionoacoustic sensor or transducer 24 is provided for sensing ionoacoustic signals, i.e. acoustic signals which are at least in part caused by energy deposition of pulses of the pulsed ion beam 14'. Both, the ultrasound transducer 22 and the ionoacoustic sensor 24 are connected with a data acquisition unit 26. The data acquisition unit may for example comprise a digital oscilloscope and secondary electronics, such as amplifiers, high-pass filters and low-pass filters. The data acquisition unit 26, in combination with the ionoacoustic sensor 24, allows for detecting the aforementioned time-resolved acoustic signals comprising an energy-deposition-signal component that is attributable to the energy deposition of an individual pulse of said pulsed ion beam 14' in the tissue of the patient 18.

In the system of FIG. 2, a trigger line 28 for conveying a trigger signal to the data acquisition unit 26 is provided. The trigger signal allows for the aforementioned determining of relative timing information of the energy deposition of the individual pulse with respect to the time resolved acoustic signal. The trigger signal indicates the arrival of the ion beam pulse in the tissue, and in this case is provided by the electronics of the chopper 16. However, similar trigger signals could also be provided by a fast detector in front of the patient 18, such as a gas detector, a semiconductor detector or a scintillation detector, or by another suitable detector for detecting secondary radiation generated by the arrival of a pulse of the pulsed ion beam 14' in the tissue of the patient 18.

Between the deposition of the ion energy in the tissue of the patient 18 by the ion pulse and the arrival of the ionoacoustic signal at the ionoacoustic sensor 24, there is a timelag corresponding to the time the ionoacoustic signal needs to propagate from its creation at the location of energy deposition to the ionoacoustic sensor 24. This time lag corresponds to the distance between the location of energy deposition and the ionoacoustic sensor 24 divided by the average speed of sound in the tissue, and therefore allows for determining the location of energy deposition. In particular, if the ionoacoustic sensor 24 is arranged on the ion beam axis or only slightly offset to it, this allows for determining information about the position along the axis of the ion beam 14 where the energy deposition per unit volume is maximum. In most applications, this is the most crucial piece of information, since other parameters defining the location of energy deposition, for example the location of the ion beam axis, the beam diameter and the like can be determined and/or controlled by other means. Nevertheless, by providing additional ionoacoustic sensors arranged in different positions (not shown in FIG. 2), in some embodiments a one-, two- or three-dimensional energy deposition distribution can be derived from the measured ionoacoustic signals.

As further shown in FIG. 2, a control system 30 is provided which is connected to receive the time-resolved acoustic signal from the data acquisition unit 26 and to subject it to post-processing, including applying a matched filter to it to thereby obtain the aforementioned filtered time-resolved signal. The control system 30 may comprise one or more microprocessors, ASICS or hardwired devices. In some embodiments, the control system 30 may be formed by a multi-purpose computer under appropriate software control. The control system 30 may comprise a single control unit, or a plurality of control units interconnected with each other. The time-resolved acoustic signal detected by the ionoacoustic sensor 24 and the data acquisition unit 26 comprises an energy-deposition-signal component that is attributable to the energy deposition of an individual pulse in the tissue, i.e. the "signal of interest", but also a strong background, collectively referred to as "noise" herein. Indeed, it is seen that the signal-to-noise ratio (SNR) in the time-resolved acoustic signal is quite low, making it difficult to clearly distinguish the energy-deposition-signal component and derive the timing information therefrom. In the filtered signal, however, the SNR is considerably increased. Accordingly, the control system 30 is further configured to derive, from the filtered time-resolved signal, occurrence timing information related to the occurrence of the energy-deposition signal component in said time-resolved acoustic signal.

In the simplest case, if the energy-deposition-signal component is a single peak, or at least comprises a unique pronounced peak, then the "occurrence" of the energy-deposition-signal component in the time-resolved acoustic signal could simply amount to the occurrence of this peak within the time-resolved acoustic signal, and the "occurrence timing information" could amount to the point in time at which this single peak is located within the time-resolved acoustic signal. However, the waveform of the energy-deposition-signal component may be more complex, and the occurrence timing information could be likewise more complex than the timing of a single peak. But at any rate, the "occurrence timing information" is timing information that represents an arrival time of the energy-deposition-signal component within the time-resolved acoustic signal. Moreover, in view of the relative timing information of the energy deposition of the individual pulse with respect to the time-resolved acoustic signal (by means of the trigger signal conveyed via trigger line 28), a delay between the energy deposition of the individual pulse and the occurrence timing information can be derived, from which the distance between the location of the energy deposition and the location of the ionoacoustic sensor 24 can be derived.

If the speed of sound within the absorptive medium was known and was constant, then this distance could be simply calculated by dividing the aforementioned delay (preferably corrected for additional delays from the trigger, the sensor and its electronics) by this speed of sound. However, particularly in medical applications, the speed of sound within tissue varies throughout the tissue and is typically not precisely known, so that because of the uncertainty in the denominator, this distance cannot be precisely derived from the delay in terms of e.g. millimeters in the real 3D space of the treatment room. However, based on this delay, this distance can be obtained very precisely relative to an ultrasound image recorded by the ultrasound transducer 22, because the ultrasound signals received by the ultrasound transducer 22, which in this embodiment is arranged directly adjacent to the ionoacoustic sensor 24, are subjected to essentially the same varying speed of sound throughout the tissue as the ionoacoustic signal. Accordingly, knowing the location of the beam axis with respect to the ultrasound image, the location of the energy deposition within the ultrasound image can be determined very precisely based on the delay between said energy deposition of that individual pulse and said occurrence timing information, and without having to know the precise distribution of speed of sound throughout the tissue.

With reference again to FIG. 2, the control system 30 hence allows for determining information regarding the location of the energy deposition within an ultrasound image recorded with said ultrasound transducer 22. A display 32 is provided in communication with the control system 30, on which a medical image of the patient 18 is displayed, including a representation 20' of the tumor, as well as an indication 34 of the location of energy deposition of the ion beam in the tissue. As is schematically shown in FIG. 2, the energy deposition can be indicated on a voxel basis, where for example the local energy dose could be indicated by color or the like. Again, as mentioned before, part of the dose distribution in the tissue can be derived from knowledge about the location of the beam axis and the beam diameter, but the critical and most challenging information needed for reconstructing this energy dose distribution is the location of the Bragg peak along the beam axis, and precisely this is provided by the shown embodiment, based on the delay between the energy deposition of an individual pulse and the corresponding occurrence timing information.

Moreover, as indicated above, rather than trying to obtain the location of the Bragg peak within 3D coordinate system associated with the radiation treatment room, it is advisable to obtain the location of the Bragg peak with respect to an ultrasound image recorded using the ultrasound transducer 22. In this regard, the medical image displayed on the display 32 may be such ultrasound image. However, the medical image displayed on the display 32 may alternatively be a further medical image that is taken with another imaging modality, and which is co-registered with the ultrasound image, including the location of the Bragg peak within said ultrasound image. This further medical image may be an x-ray image or an MRT image, which may be taken during the radiation therapy treatment, or which may have been taken prior to this treatment, for example for the purposes of radiation treatment planning.

FIG. 2 further shows a control line 36 connecting the control system 30 with the ion accelerator 12 and the chopper 16. Via the control line 36, the control system 30 may control the ion accelerator 12 with respect to the ion energy, and may control the chopper 16 to provide desired pulse lengths, as described in more detail below. In addition, the control system 30 is connected to a database 38 which previously generated templates for use in a matched filter in a manner described below are stored. Finally, a treatment table 40 is schematically shown, on which the patient 18 is supported. The treatment table 40 is connected with the control system 30 via a further signal line 42 allowing for conveying positioning parameters for the treatment table 40.

Figure 4:
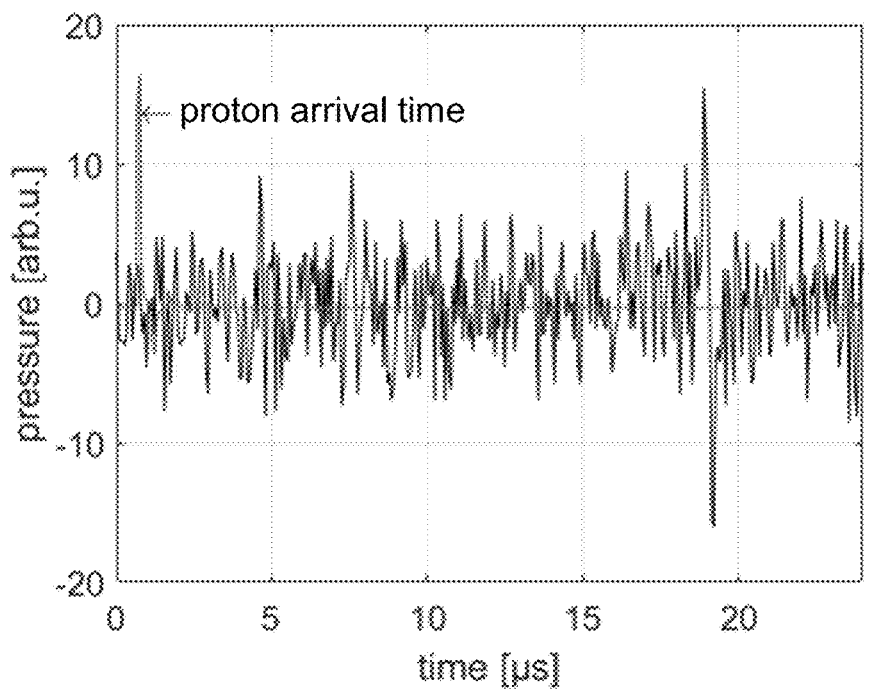
FIG. 4 shows a time-resolved acoustic signal of 20 MeV proton beam impinging a water phantom recorded with an ionoacoustic sensor FIG. 5A-D each show a compression curve and a rarefaction curve and the sum of compression and refraction curves for pulse durations of 50 ns, 160 ns, 500 ns and 1 µs, respectively for 20 MeV protons.
Figure 5A:
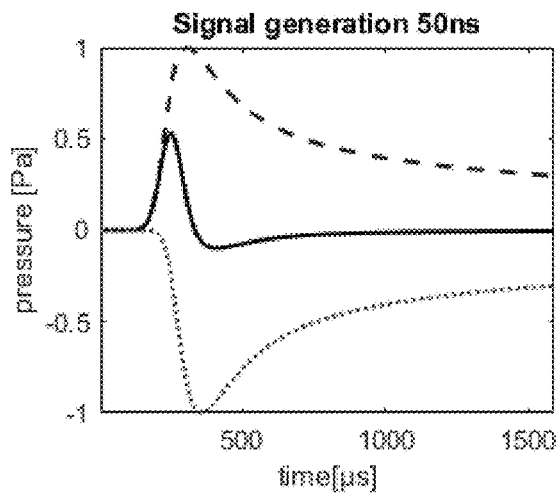
Figure 5B:
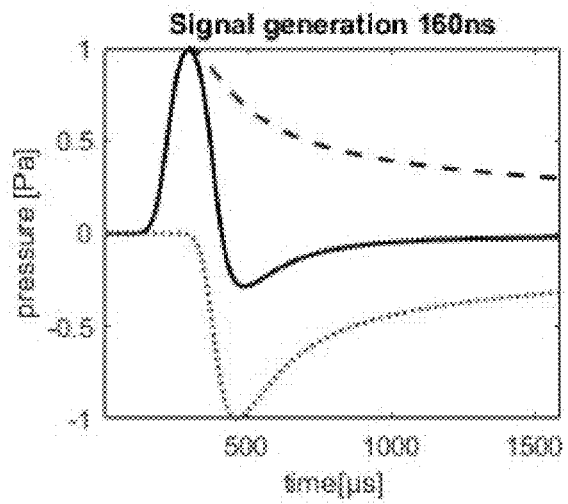
Figure 5C:
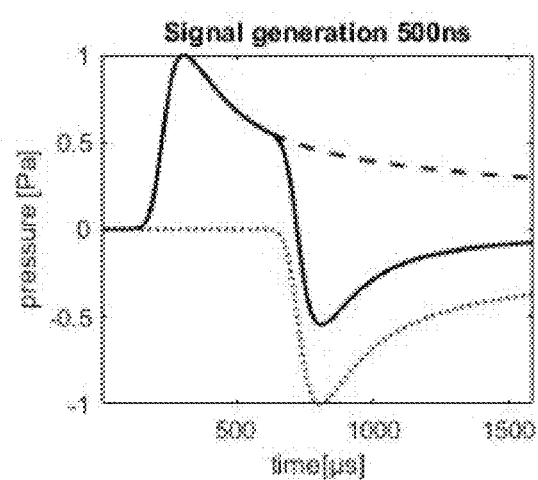
Figure 5D:
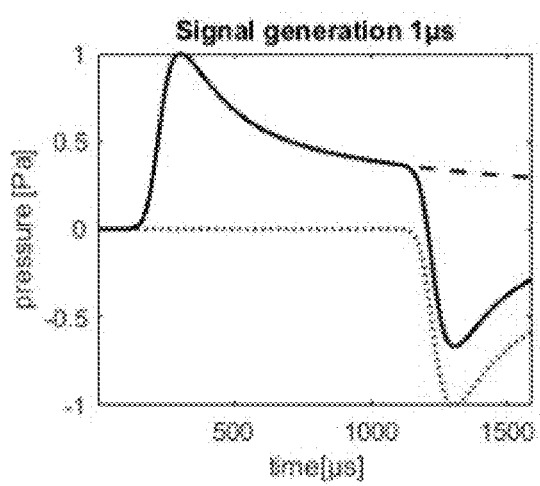

FIG. 4 shows an example of a time-resolved acoustic signal recorded with the ionoacoustic sensor 24 and the data acquisition unit 26. This time-resolved acoustic signal comprises an energy-deposition-signal component having a pronounced peak (highlighted by "proton arrival time" in FIG. 4, corresponding to the "occurrence timing information" referred to above), but also obviously has a large noise component. Indeed, the SNR in this case is so poor that it is difficult to clearly distinguish the energy-deposition-signal component from the background, and to reliably derive the occurrence timing information therefrom.

According to the invention, the time-dependent acoustic signal is subjected to post-processing by the control system 30, which post-processing includes applying a matched filter, to thereby increase SNR and to facilitate detecting the energy-deposition-signal component within the time-resolved acoustic signal.

A matched filter maximizes the SNR of a measurement for a known signal shape. One way of applying the matched filter to the time-resolved acoustic signal may comprise correlating the expected signal shape, also referred to as the "template", with the time-resolved acoustic signal. The ideal filter (or template) T(t) is identical to expected signal, i.e. to the energy-deposition-signal component. The resulting correlation function maximizes SNR and peaks at the position of best overlap of the template and the signal. For discretized signals, a normalized correlation $CC_{M,T}(\tau)$ can be expressed as:

$$CC_{M,T}(\tau) = \frac{\sum_t M(t) \cdot T(t+\tau)}{\sqrt{AC_{M,M}(0) \cdot AC_{T,T}(0)}}$$

Herein, M(t) is the measured signal, T(t) is the template and T is the time shift between the two functions. The normalization in the denominator consists of the auto-correlation functions of the measurement $AC_{M,M}$ (o) and the template $AC_{T,T}$ (o) at zero lag and ensures a range of correlation values between −1 and 1.

The challenging part of applying the matched filter obviously is to determine the appropriate template for the radiation situation at hand. As the skilled person will appreciate, matched filters for this are used in the art when the waveform of the signal of interest is known, but in the art, it is not known precisely how the signal of interest, i.e. the energy-deposition-signal component would actually look like in practice. The inventors could however confirm that useful templates representing a predicted waveform of the energy-deposition-signal component can be obtained by computer simulations. In addition or in the alternative, useful templates can be obtained by measuring the signal in a phantom of similar geometry as in the patient with same beam parameters and center, but using higher doses than applicable in a patient.

One part of the computer simulation comprises simulating the 3D dose distribution of the ion beam in the absorbing medium and deriving the pressure distribution caused thereby. The dose distribution can for example be calculated using the FLUKA code described in A. Ferrari et al. FLUKA: A Multiple-Particle Transport Code. Technical report, Stanford linear accelerator Center (SLAC), Menlo Park, CA, December 2005 and in T. T. Böhlen et al. The FLUKA Code: Developments and Challenges for High Energy and Medical Applications.

Nuclear Data Sheets, 120:211 to 14, June 2014. The inventors derived 3D dose distributions from proton beams in water using FLUKA with 50×106 particles and a grid spacing of 20 m. The resulting average dose deposition per proton was then scaled by the number of protons per pulse derived from a Faraday cup measurement next to the beam exit window and the respective pulsing structure. Assuming no heat defect, the deposited dose was multiplied by the mass density (998.1 kg/m$^3$) and the Grüneisen parameter (0.108 at 20.1° C.) to obtain the initial pressure distribution in Pa.

In a consecutive step, acoustic waves associated with this initial pressure distribution can be simulated. For this purpose, existing software tools can be used for simulating the propagation of waves, for example the Matlab toolbox "k-wave". For the initial simulation carried out by the inventors, a sound speed $v_s$ in water of 1482 m s$^{-1}$ and an idealized point sensor 25.4 mm away from the Bragg peak was assumed.

The ionoacoustic pressure wave is believed to arise from two different components—the temporal heating function $H_t(t)$ and the spatial heating function $H_s(r', \theta', \varphi')$, which are given by the energy converted per unit time and space, respectively. $H_t(t)$ is thus closely related to the beam current I(t) (see FIG. 3), while Hs(r', θ', φ') is a 3D description of the Bragg curve as seen from the position of the transducer. A detailed description of the underlying physics can be found in Jones et. al. How proton pulse characteristics influence protoacoustic determination of proton-beam range: simulation studies. *Physics in Medicine & Biology*, 61 (6): 2213, 2016, and shall not be repeated here. The pressure at the position of the transducer at time t is given by the convolution of the temporal heating function $H_t(t)$ with the core of the spatial heating function $P_\delta(t)$:

$$p(t) = \frac{\partial}{\partial t} \int_{-\infty}^{\infty} H_t(t-\tau) P_\delta(\tau) d\tau = \left[\frac{\partial H_t(t)}{\partial t} * P_\delta(t)\right]$$

$P_\delta(t)$ is proportional to a spherical surface integral over the spatial heating function with the detector at the center:

$$P_\delta(t) = \frac{1}{v_s t} \frac{v_s \beta}{4\pi C_p} \int_0^{2\pi} \int_0^{\pi} d\theta' d\phi' R'^2 \sin(\theta') H_s(r', \theta', \phi')$$

Herein, variables with prime symbol refer to the coordinate system of the detector. Thus Hs(r', θ', φ') is the spatial heating function as seen by the detector and $P_\delta(t)$ is calculated for the position of the detector. $R' = v_s \cdot t$ is the distance from the source to the detector which enables a direct translation from distance to time and vice versa via the acoustic wave velocity $v_s$ within the medium, here water. β is the thermal coefficient of volumetric expansion and Cp is the specific heat capacity at constant pressure as usual.

For rectangular pulse shapes, which is a good approximation to the pulse shape as shown in FIG. 3, $\partial H_t(t)/\partial t$ collapses into two delta-like peaks—a positive one when the beam is turned on (compression) and a negative one when the beam is turned off (rarefaction). FIG. 5A-D show simulations of ionoacoustic signals generated in the described manner by varying pulse durations with rectangular shape. In order to generate 1 Pa of pressure, the beam current was set to 320 nA for 20 MeV protons and the distance of the Bragg peak to the transducer was 25.4 mm. The beam was assumed to have a radially symmetric cross-section with a Gaussian dose distribution of σ=1.3 mm. The influence of transducer characteristics on the signal is for the time being neglected in these simulations, but will be discussed separately below.

In each of FIG. 5 A-D, the dashed curve is a compression curve that is created when the beam is turned on and the dotted curve is a rarefaction curve which is generated when the beam is turned off. The delay relative to the compression curve is equal to the pulse durations of 50 ns (FIG. 5A), 160 ns (FIG. 5B), 500 ns (FIG. 5C) and 1 μs (FIG. 5D), respectively. The sum of the compression and rarefaction curves results in the total temporal pressure distribution at the detector position, shown by the solid line, and represent a prediction of the ionoacoustic signals to be detected. Focusing on these signals, the rising slope results from the slope of the spatial heating function when observing the acoustic wave in axial direction distal to the Bragg peak. It is closely related to the slope of the dose profile beyond the Bragg peak. For short pulses up to 160 ns the rarefaction signal destructively interferes with the compression and the overall amplitude is reduced. For pulses longer than that, the maximum amplitude stays unaltered, although the total deposited energy increases. The maximum negative amplitude becomes slightly more negative with increasing pulse duration. The principle form of the acoustic waves was found to not change when higher proton energies are used, but the timescale extends as the Bragg peak becomes wider.

The inventors could confirm that in order to generate a realistic simulation of the energy-deposition-signal component, the transducer characteristics of the ionoacoustic sensor 24 should be taken into account. Previous studies have shown that for transducers of the type employed by the inventors, the transducer transfer function can be approximated by a Butterworth band-pass filter of first order with the lower and upper cutoff frequency coinciding with the −6 dB bandwidth of the utilized transducer (2.2 MHz-4.7 MHz), as described e.g. in Assmann et al.: "Ionoacoustic characterization of the proton bragg peak with submilliliter accuracy" in *"Medical physics"*, 42(2):567-574, 2015.

Figure 6:
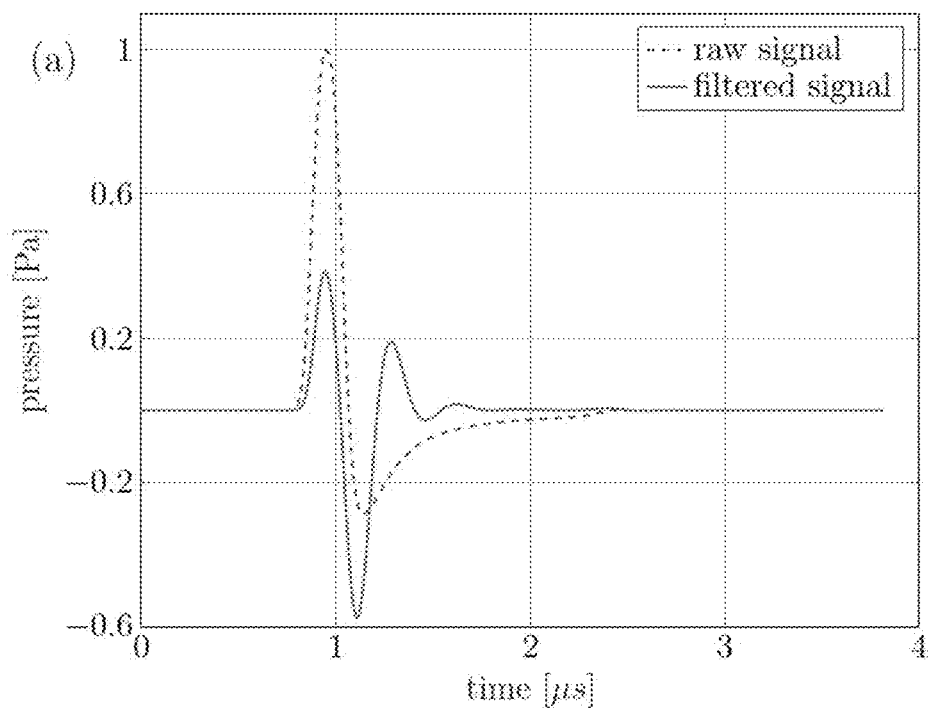
FIG. 6 shows a template for an energy-deposition-signal component wave form obtained by simulation and a fitted version accounting for the transducer characteristics.

The influence of the transducer transfer function on the simulated template for the energy-deposition-signal component waveform is illustrated in FIG. 6 showing both, the simulated template (dashed line) as well as a modified version thereof, which accounts for the transducer characteristics, for a ionoacoustic signal generated by 20 MeV protons and a rectangular pulse of 160 ns duration. As can be seen from FIG. 6, the transducer characteristics influence the amplitude, the frequency content and its phase. More particularly, the transducer used to detect the pressure wave distorts the frequency content and the amplitude of the original ionoacoustic signal due to its limited bandwidth. The short duration of the signal in time domain (~600 ns for 20 MeV protons), induces a broad frequency spectrum and the limited bandwidth of the transducer causes frequencies outside the sensitive range to be attenuated.

In addition, the transducer's geometrical properties also have an influence on the detected signal. The sensitive surface area of the transducer can be interpreted as infinitely many point detectors arranged together. A recorded signal can thus be seen as an average over all point detectors. The measured signal shape and amplitude therefore depend on the position and the angle of the detector relative to the source and the spatial averaging over the surface area. For the simulations shown in FIG. 6, a perfectly axially aligned detector with no angular offset was assumed. The effect of spatial averaging can be mitigated with a focused detector which is comprised of a concave sensitive area such that the spherically expanding pressure wave is arriving at the complete sensitive surface of the detector at the same time. Using a focused sensor (transducer) requires precise positioning of the transducer to keep distortions low. An active change in orientation or a shift of the transducer changes spatial averaging and hence the recorded signal. All stated effects can be incorporated in the Butterworth bandpass filter used to approximate the transducer's transfer function in the present embodiment. As mentioned before, the Butterworth filter is just one possibility to approximate the transducer transfer function. Other types of bandpass filters are likewise possible. Moreover, it is also possible to obtain the transfer function in a dedicated measurement. The simulated and filtered signal shown in FIG. 6, as well similar signals obtained for other pulse durations of the ion beam, were then used as templates for a matched filter, in this case employing the correlation filtering process described above.

Figure 7:
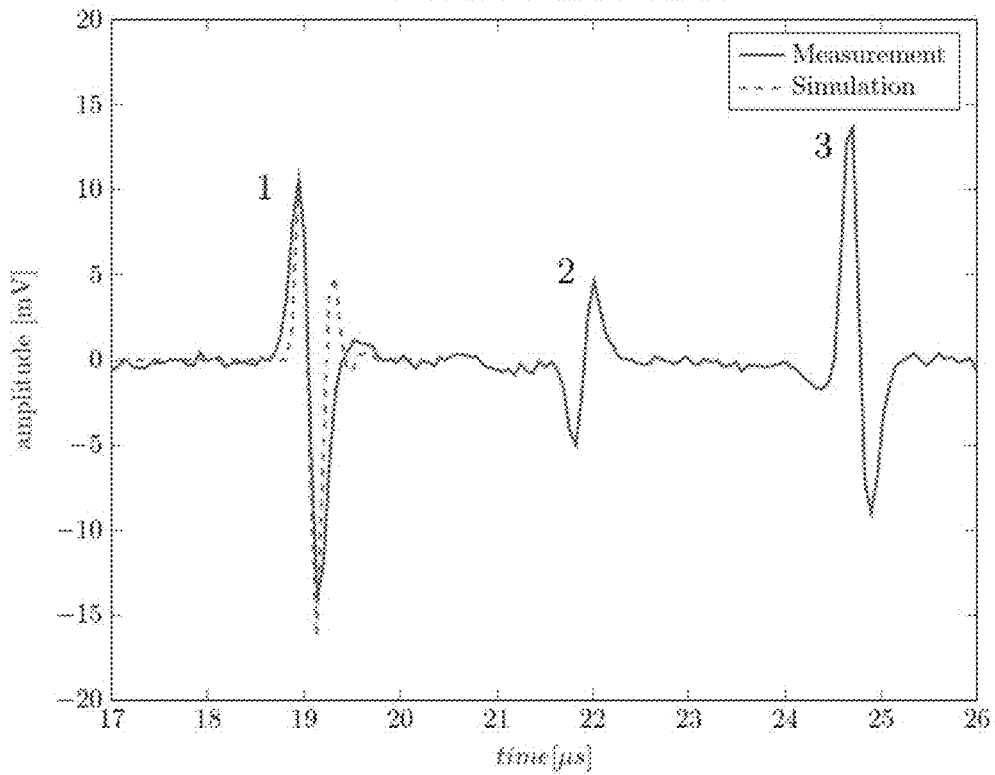
FIG. 7 shows measured ionoacoustic signals from 20 MeV protons in water averaged from 200 measurements, and the template of FIG. 6 for comparison.
Figure 8A:
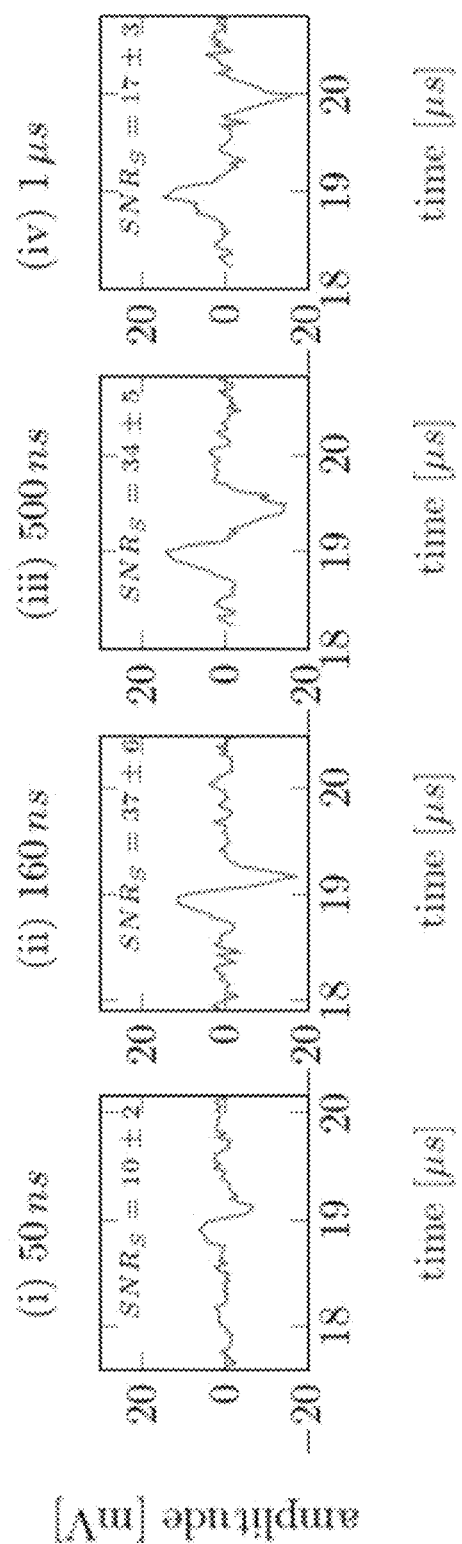
FIG. 8(a) shows time-resolved acoustic signals from 20 MeV protons in water generated at different pulse lengths.
Figure 8B:
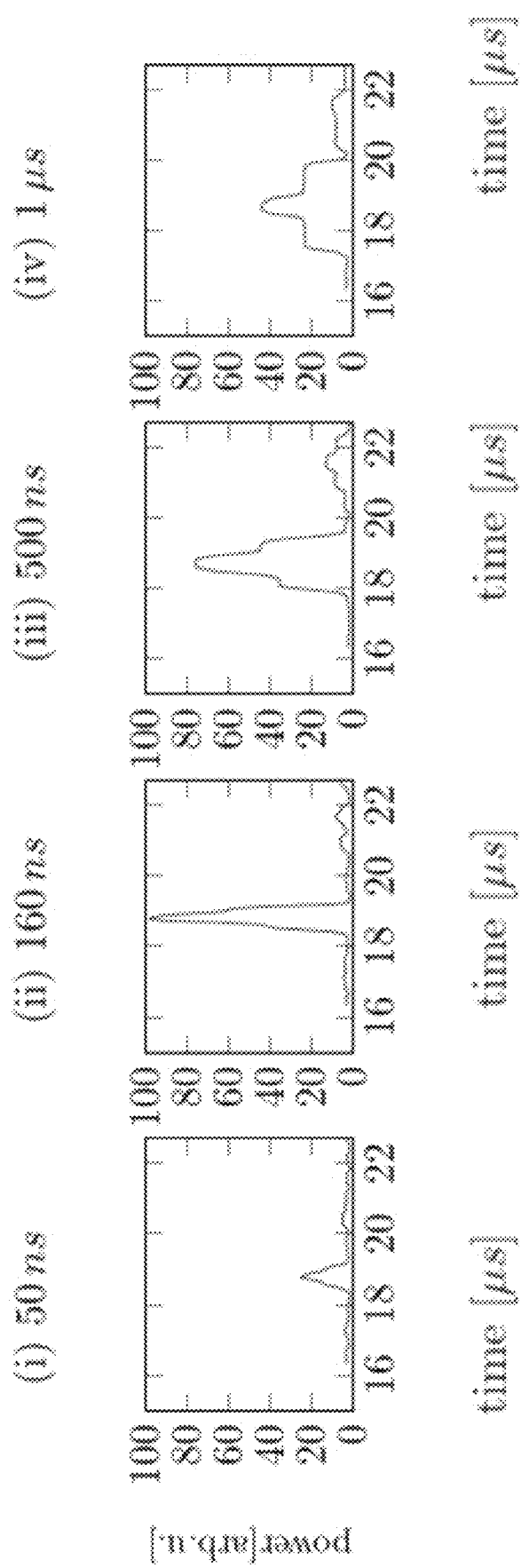
FIG. 8(b) shows the corresponding moving average power spectrum of the signals of FIG. 8(a)
Figure 8C:
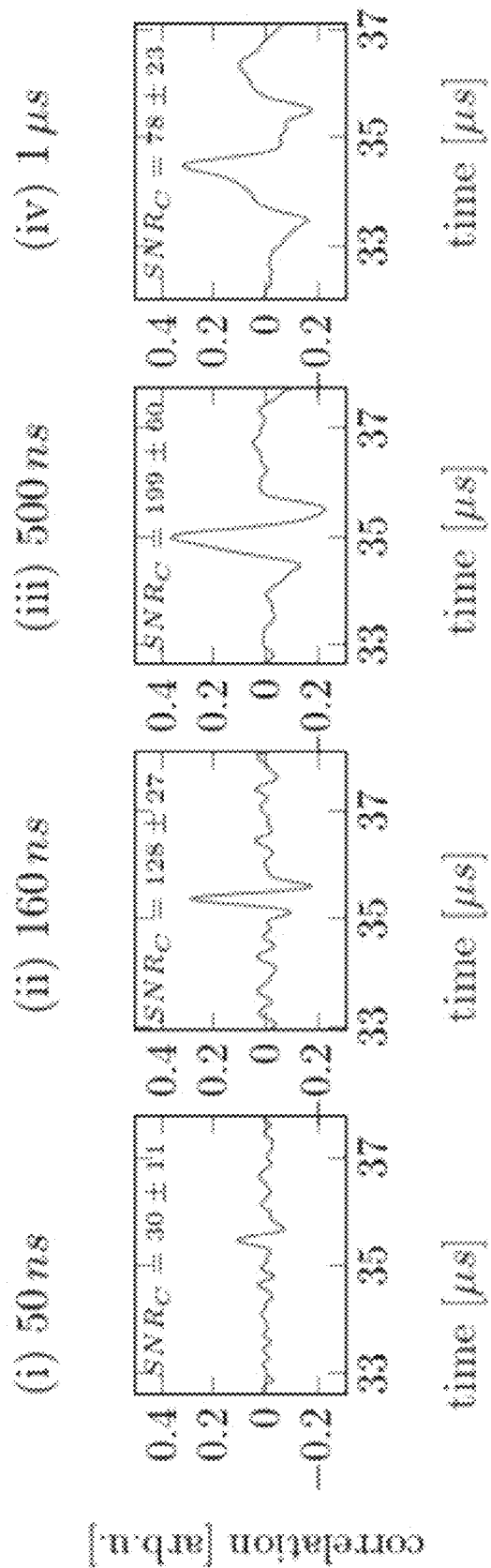
FIG. 8(c) shows filtered time-resolved acoustic signals generated at different pulse lengths.
Figure 8D:
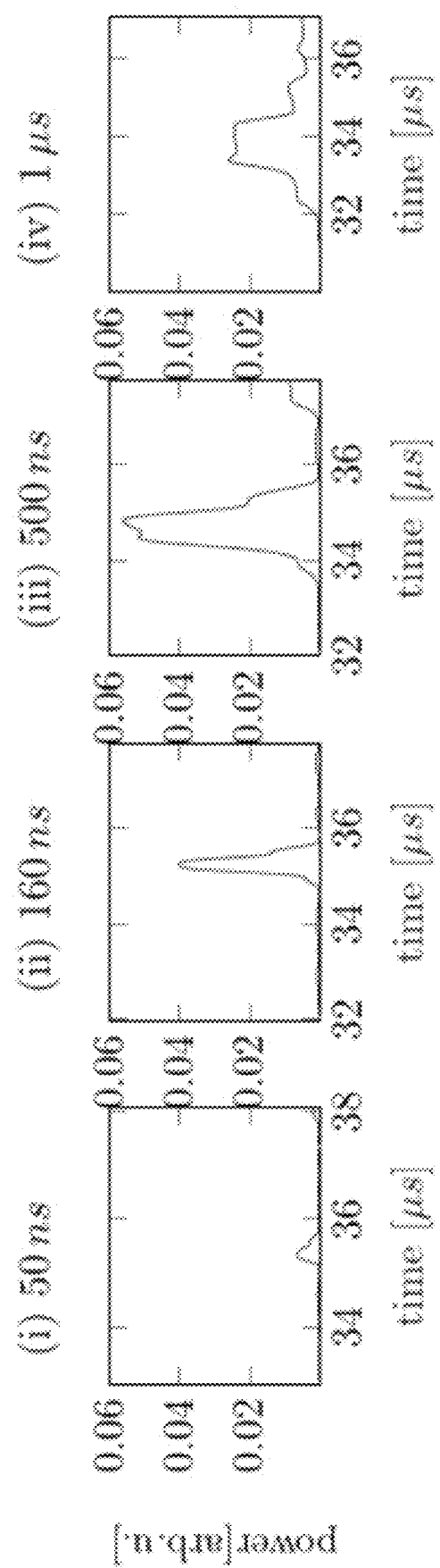
FIG. 8(d) shows the moving average power spectrum of the filtered signals of FIG. 8(c).

To put the simulation shown in FIG. 6 in perspective, an ionoacoustic measurement with high integral dose (128 Gy peak dose) was carried out, with the result shown in FIG. 7. The signal is generated by 20 MeV protons and a rectangular heating function (proton pulse) of 160 ns duration. The beam current was 4.5 µA, and the ionoacoustic signal was averaged from 200 measurements. The simulation from FIG. 6 (including the filtering to account for the transducer characteristic) is plotted in addition for a better comparison. The measurement in FIG. 7 shows three distinct signals. The first signal (1) is the aforementioned energy-deposition-signal component which is caused by the ultrasound waves traveling from their origin at the Bragg peak to the transducer. This is the type of signal whose structure was discussed in FIG. 5A-D.

The third signal (3) is a reflection signal which is a mirrored and phase inverted copy of the direct signal. It is caused by the ultrasound waves traveling backwards from the Bragg peak and being reflected at the entrance window of the water tank used in the experiment. The second signal (2) is caused by the beam entering the water tank through the entrance window. Note that these signals will obviously not be present in a measurement carried out on a patient, but are useful for understanding the underlying physical mechanisms.

In addition, FIG. 7 shows the similarity between the measurement and the simulation of the energy-deposition-signal component. The simulation has a slightly higher frequency content and overestimates the second maximum of the signal. A possible reason for this dissimilarity are potential misalignments of the transducer from the ideal axial position with zero angular offset. This deviation could be corrected by adjusting the filter boundaries of the Butterworth band-pass filter. However, in realistic applications the signal shape is generally not known in such detail and the simulation can therefore not be adjusted according to the measurement. Rather, the simulation must already be determined in advance, consisting exclusively of information known before the measurement is recorded.

The standard procedure to determine the measurements quality is calculating the SNR. It is defined as the average signal power divided by the average noise power. For discretised signals the SNR is given as:

$$SNR = \frac{P_{signal}}{P_{noise}} = \frac{\frac{1}{N}\sum_{n=1}^{N} A_{signal}^2(n)}{\frac{1}{M}\sum_{m=1}^{M} A_{noise}^2(m)}$$

Here, $A_{signal}(n)$ and $A_{noise}(m)$ are the amplitudes of the signal and the noise respectively, n are all samples considered for the calculation of the signal power and m are all samples considered for the calculation of the noise power. N is the total number of samples within the signal and M is the total number of samples within the noise region which is defined before the arrival of the signal. In the following, $SNR_S$ is used when referring to the SNR of the raw ionoacoustic signals and $SNR_C$ is used to describe the SNR of the filtered signals after applying the matched filter, in the present case, after performing the correlation as stated above.

FIG. 8 (a) shows four different ionoacoustic signals generated by single rectangular proton pulses of increasing pulse duration and their "moving average power spectra" needed for $SNR_S$ calculation in panel (b). Panel (c) shows the measurement after applying the matched filter and (d) shows the moving average power spectra of the after the matched filter was applied. The details of each panel are discussed in the following.

Four different ionoacoustic measurements (time-resolved acoustic signals) generated by 20 MeV protons and pulse durations of 50 ns, 160 ns, 500 ns and 1 µs at a beam current of 4.5 µA are plotted in FIG. 8 (a). Shown are 5 averages each, which according to FLUKA Monte Carlo simulations corresponds to a peak dose value at the Bragg peak between 1 Gy and 20 Gy, depending on the pulse duration. The signal amplitude almost doubles between 50 ns and 160 ns while it only increases negligibly for higher pulse durations, which is consistent with the simulations shown in FIG. 5A-D.

Panel (b) of FIG. 8 shows the corresponding moving average power spectra of the signals of FIG. 8 (a). The moving average power spectra are needed for determining the $SNR_S$ for each of the measurements and are calculated as follows: The duration d of the signal was determined using the simulated signals of FIG. 6 and similar signals obtained for the further pulse durations, to thereby avoid a dependency on noise fluctuations. A threshold of 20% of the maximum amplitude within the rising edge of the signal was determined as the starting point of the signal. To determine the endpoint of the signal correspondingly, a 20% threshold of the minimum amplitude occurring after the minimum of the signal was used. The expected duration of the signal could then be determined by the difference of these time points. The average power over that period of time was calculated for every possible location within the measured time frame as follows:

$$\bar{P}(n) = \frac{1}{d}\sum_{n}^{n+d} A_{signal}^2(n)$$

Herein, $\bar{P}(n)$ is the moving average power spectrum and $A_{signal}$ is the amplitude of the signal. $\bar{P}(n)$ peaks when the time interval perfectly overlays with the signal position (8 (b)). From this moving average power spectrum the $SNR_S$ values shown in FIG. 8 (a) were obtained by dividing its peak value by the average noise value. The interval taken into account for the calculation of the noise power was chosen to end before the arrival of the first signal as shown in FIG. 7, i.e. before the arrival of the energy-deposition-signal component, to exclude possible secondary signals and reflections. Further, the duration of that interval was maximized within the measured time frame ensuring the most accurate estimate of the average noise power. The $SNR_S$ depicted in panel (b) of FIG. 8 increase between signals corresponding to 50 ns and 160 ns, which is due to the increase in amplitude of the energy-deposition-signal component as apparent from FIGS. 5A-D, and then decreases again. The decrease is due to the fact that the energy-deposition-signal component generated by a 500 ns pulse is longer but not higher in amplitude than that for the 160 ns case and so the average signal power drops.

A correlation-based evaluation was used to filter and denoise the measurements. The filtered signals are shown in FIG. 8 (c). Being a simulation of the expected signal, the template T contains all the known information about the signal shape. Such a "matched" filter allows to optimally harvest prior information by means of (in-silico) simulations performed upfront. For every possible time shift T of the template relative to the measurement, the correlation function $CC(\tau)$ is calculated. This correlation function maximizes at the location where the time-resolved acoustic signal obtained by the measurement and the template overlap best, giving rise to the information where the energy-deposition-signal component can be found within the time-resolved acoustic signal measurement (FIG. 8 (c)), i.e. the aforementioned "occurrence timing information" related to the occurrence of the energy-deposition-signal component in the time-resolved acoustic signal.

The $SNR_C$ of the correlation functions shown in FIG. 8 (c) were calculated similarly to the $SNR_S$ of the measurements as described above. The moving average power spectra of the correlation functions are needed for the calculation of the $SNR_C$ (FIG. 8 (d)). The duration of the signal was determined by auto-correlating the template and choosing the adjacent zero-crossings next to the main peak as the starting point and end point of the signal. To minimize the influence of beam current fluctuations, the displayed $SNR_C$ in FIG. 8 (c) are mean values which were calculated after repeating the $SNR_C$ calculation procedure 100 times and averaging the 100 $SNR_C$.

The $SNR_C$ increases more than 4-fold from 50 ns to 160 ns, which is due to the increase in amplitude within the underlying signals. Between 160 ns and 500 ns there is an additional increase in $SNR_C$ even though the unfiltered measurements show a slight decrease in $SNR_S$. The reason for the $SNR_C$ increase is the fact that the maximum possible $SNR_C$ of a correlation function depends on the total energy of the input signal, as is e.g. explained in George Turin, "An introduction to matched filters", IRE transactions on information theory, 6 (3): 311-329, (1960). The $SNR_C$ of the correlation functions hence increases due to the increase in signal energy in the 500 ns case as compared to the 160 ns case. For the correlation function of the 1 μs case, the $SNR_C$ drops again, which is mainly due to the fact that the lower frequencies within the underlying measurements cause the correlation peak to broaden and therefore reduces its average power.

It is seen from the above that the pulse duration influences the applied dose, the $SNR_S$ and the $SNR_C$. The dose increases linearly with the pulse duration and is, in a clinical context, determined in the treatment planning process. In contrast to the dose, the SNR increases rapidly for short pulse durations before reaching maximum within a plateau region and declining for even longer pulse durations. The ideal pulse duration, which is found for a maximized SNR at a constant dose limit, can be found using a dose limited SNR, referred to as $SNR_D$ herein, which is defined as $SNR_D = SNR/D$, wherein D represents the dose. This normalization by the dose D may also be understood as the increased number of averages possible for signals of shorter pulse durations compared to longer ones at a given dose limit.

The maximum of this dose limited $SNR_D$ describes the ideal tradeoff between applied dose and SNR. To determine the ideal pulse duration for ionoacoustic signal generation, the $SNR_D$ of signals generated with constant beam current and varying pulse durations recorded in an axial measurement position is shown in FIG. 7. The lower curve shows the $SNR_{D,S}$ of ionoacoustic signals as a function of pulse duration and a given dose of 1 Gy. The upper curve shows the corresponding $SNR_{D,C}$ of the correlation functions, i.e. matched filtered time-resolved acoustic signal for the same dose limit.

Figure 9:
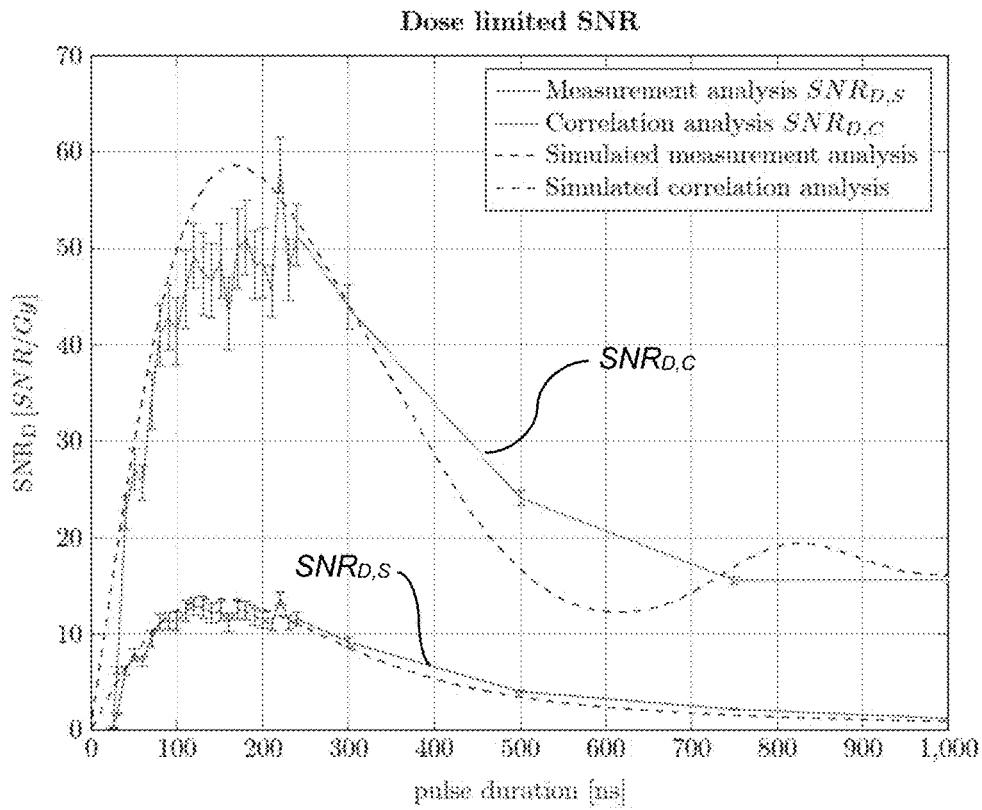
FIG. 9 shows simulated and measured dose-limited SNR values for 20 MeV protons in water.

The dashed curves in FIG. 9 show the corresponding simulations of the $SNR_D$-values. Ionoacoustic signals including transducer specific properties, i.e. templates have been simulated and their average signal power was evaluated. The noise power was assumed to be independent of the pulse duration and therefore constant. This constant noise floor was chosen such that the simulation best matches the measured data. For the correlation analysis the simulated signals were auto-correlated and the average signal power of the auto-correlation functions was obtained as signal power. For the noise power calculation, the templates were correlated with the external noise measurement, since the average noise power of the correlation functions is proportional to the signal energy of the template.

It is seen that the dose limited SNR ($SNR_D$) of the filtered time-resolved signal exceeds that of the raw detected time-resolved acoustic signal by a factor 3 for short pulse durations (e.g. 50 ns) and up to a factor 6 for long pulse durations (e.g. 500 ns). This increase is directly proportional to the contained signal energy of the raw measurements, which continuously increases up to the longest investigated pulse duration of 1 µs. The dependency on the total signal energy also causes the slight shift of the ideal pulse duration of the simulations—from 150 ns when considering only the raw time-resolved acoustic signal up to 170 ns for the correlations (filtered time-resolved signal).

In the example shown above, the simulation of said template as an ionoacoustic signal was carried out in water rather than in a digital representation of tissue of a patient. However, the methods employed so far can be extended to the generation and propagation of the ionoacoustic signals in actual patient tissue, based on space-resolved information about mass density and/or speed of sound in said tissue. With this space-resolved information, the propagation of the ionoacoustic signal through the tissue can be simulated more realistically, and the waveform of the energy-deposition-signal component can be predicted with more precision. The space-resolved information may be obtained from medical images obtained during for the purposes of treatment planning, but it can also be obtained from medical images taken during the radiation therapy. From these medical images, information regarding the mass density and/or speed of sound can be discerned. As explained in the introductory portion of the specification, in such medical images, and in particular in combinations of medical images, different types of tissue, fat, water, bone and the like can be identified, for which mass density and said speed of sound are at least approximately known.

In further embodiments, it is possible to subject the template to a self-adapting and/or self-optimizing procedure, in order to more realistically represent the energy-deposition-signal component at the detection apparatus. In this scenario, a preliminary template is generated by computer simulation e.g. using the techniques described above, and subsequently improved such as to lead to improved filtering. In particularly useful embodiments, the self-adapting and/or self-optimizing procedure comprises varying the time length of the template such as to maximize the SNR, as was explained in the introductory portion of the specification.

It is also possible to optimize the template in an iterative procedure, to thereby increase the SNR. Herein, the optimization can again involve choosing an optimum time length of the template, i.e. a time length that leads to the largest SNR.

In a different approach, the template may be selected from the database 38 of previously generated templates as schematically represented in FIG. 2. As explained above, the previously generated templates may comprise templates which have been obtained on nonliving samples using much higher doses than those possible in clinical applications, thereby leading to better SNR of the time-resolved acoustic signals.

Such selected templates can be further modified to account for the shape of the individual ion pulse and/or the sensor characteristics. The rationale behind this approach is that knowing how the actually used ion pulse differs from the ion pulse that was used for generating the previously generated templates in the database 38, the template can be modified such as to better match the present situation with the ion pulse shape actually used. The same is true for the characteristics of the sensor that is used for detecting the time-resolved acoustic signal, such as the aforementioned transducer. The influence of the present sensor characteristics on the measured time-resolved acoustic signal can be accounted for by modifying the selected template accordingly, for example by applying a suitable filter to the selected template.

In the preceding section the maximum possible SNR of ionoacoustic signals and the corresponding pulse duration for a dose limited measurement with fixed beam current was examined. However, if the beam current is a free parameter, SNR can also be elevated by increasing the beam current as a whole. The total dose deposition can still be kept constant by reducing the number of pulses and hence the number of measurements taken into account for averaging.

Figure 10:
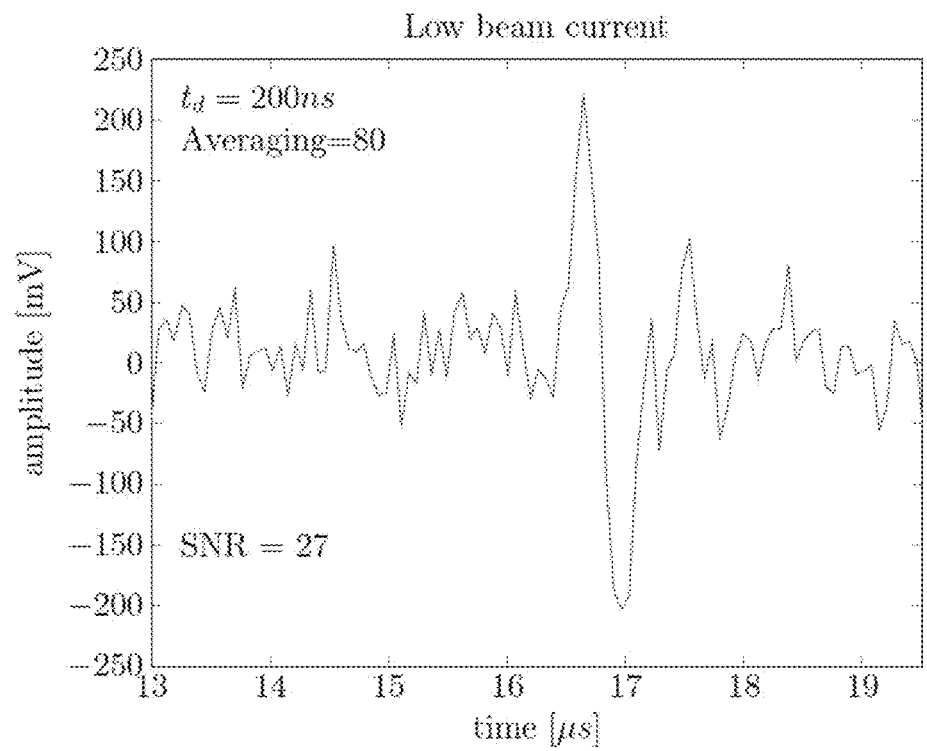
FIG. 10 shows 80 summed measurements of time-resolved acoustic signals with a beam current of 0.65 µA of 20 MeV protons impinging on a water phantom.
Figure 11:
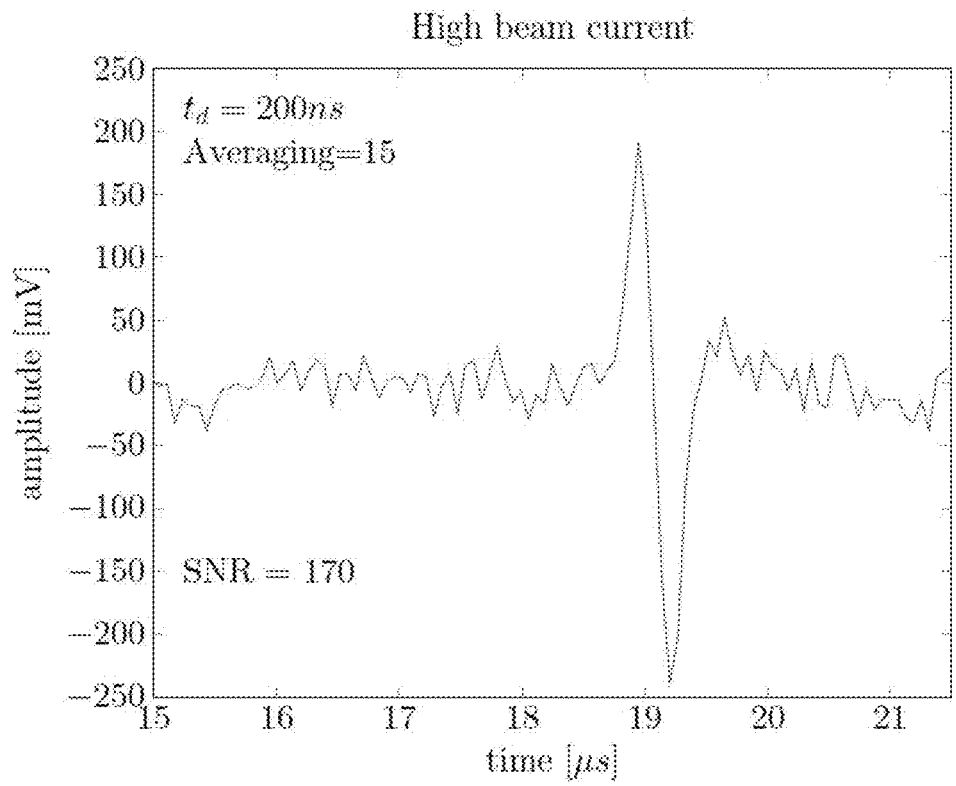
FIG. 11 shows 15 summed measurements of time-resolved acoustic signals with a beam current of 4.5 µA of 20 MeV protons impinging on a water phantom.

FIG. 10 shows 80 summed measurements of time-resolved acoustic signals with a beam current of 0.65 µA, resulting in a dose of 0.15 Gy per pulse, and therefore an accumulated peak dose of 12 Gy. FIG. 11 shows 15 summed measurements with a beam current of 4.5 µA resulting in 0.8 Gy per pulse accumulating the same integral peak dose of 12 Gy. The measurements here have been summed rather than averaged to show the similar signal amplitude and simplify comparison. Due to the higher beam current, the $SNR_S$ could be improved from 27 in the first case to an $SNR_S$ of 170 in the second. This $SNR_S$ increase through increasing the beam current at fixed total dose directly translates to the corresponding $SNR_C$. For both of the measurements shown in FIGS. 10 and 11, the correlation (i.e. applying the matched filter) would again improve the SNR by roughly a factor of 3.5. This clearly shows that a high beam current is beneficial for the generation of ionoacoustic signal having a high SNR, under the constraint of a given dose limit.

The reason for this increase in SNR may be explained as follows: the amplitude of the ionoacoustic signal is directly proportional to the number of particles per shot and thus directly proportional to the beam current. The noise, however, is not affected by the beam current. Doubling the number of particles in a measurement by increasing the beam current will thus lead to an increase in amplitude by a factor of 2 and therefore an $SNR_S$ increased by a factor 4, since the $SNR_S$ is calculated from the moving average power spectra which includes squaring. Averaging several measurements, on the other hand, will leave the ionoacoustic signal amplitude unchanged. Due to the statistic nature of noise, the noise floor will reduce by the square root of the number of measurements averaged. Doubling the number of particles by averaging two measurements which only differ in noise will therefore decrease the noise floor by $\sqrt{2}$ and therefore only increase the $SNR_S$ by a factor 2. This beam current dependency hence favors high beam currents. If and to the extent that beam current can be adjusted, the beam current can be increased up to the limiting case where the whole dose is delivered in a single shot.

Starting from a single shot of ideal pulse duration as described in the previous section, the question arises if a further reduction in pulse duration is useful in order to enable an even higher beam current at a constant dose. The inventors could confirm that this is indeed the case, as can be discerned from FIG. 12 discussed below.

Figure 12:
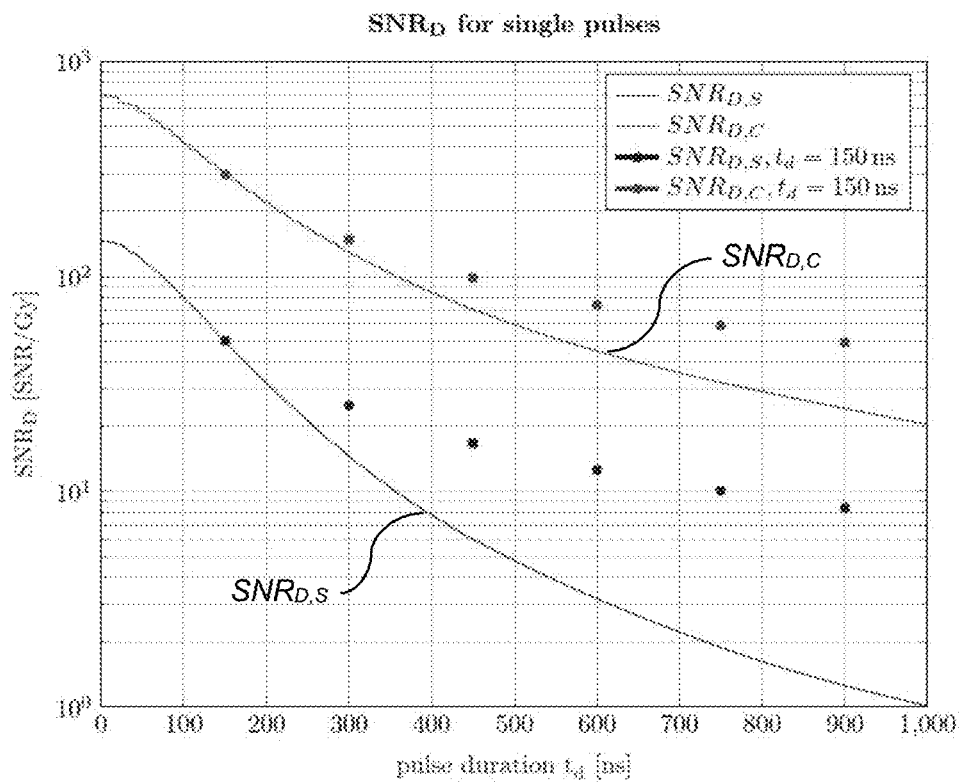
FIG. 12 shows $SNR_{D,S}$ and $SNR_{D,C}$ of non-averaged signals simulated for different pulse durations of 20 MeV protons in a water phantom.

FIG. 12 shows $SNR_{D,S}$ and $SNR_{D,C}$ of non-averaged signals generated for different pulse durations (solid lines). For each pulse duration, the beam current is inversely chosen such that in each case, a same, fixed dose limit is obtained. For these simulations, transducer characteristics have been neglected for simplicity and a dose limit of 1 Gy was assumed. Further, Gaussian pulse shapes were assumed since for very short pulse durations the approximation of infinitely short rise times within a rectangular pulse fails and would distort the results.

From FIG. 9 it was seen that for optimizing the SNR, for a given beam current, a pulse duration $t_d$ of about 150 ns would be optimum in case of 20 MeV protons. However, it is seen from FIG. 12 that if the beam current can be further increased, allowing for shorter pulse durations for delivering the same dose of 1 Gy, both $SNR_{D,S}$ and $SNR_{D,C}$ can be significantly increased, although the results of FIG. 9 would suggest that the shorter pulse durations would per se lead to slightly less favorable values. However, it is to be kept in mind the FIG. 9 only shows $SNR_{D,S}$ and $SNR_{D,C}$ for a given beam current, but from FIG. 12 is apparent that an increased beam current outweighs the optimum pulse duration. So it is seen that for increasing the SNR of the ionoacoustic measurement, the beam current should be chosen as high as possible.

However, in many cases the beam current cannot be freely chosen. If only smaller beam currents are available, the further question arises whether a given dose should be applied in a single, longer pulse or in a set of shorter pulses having an optimum pulse length for an increased SNR. In view of the lessons learned from FIG. 9, the inventors concluded that for a given beam current, the SNR could be increased if instead of one long pulse, the same dose is delivered in a set of shorter pulses, having a pulse duration that is chosen for optimizing $SNR_{D,S}$ or $SNR_{D,C}$ as shown with reference to FIG. 9 above.

This is further confirmed by the data shown in FIG. 12. The additional crosses indicate the expected $SNR_{D,S}$ and $SNR_{D,C}$ that would be obtained if longer pulses with pulse durations corresponding to multiples of 150 ns (i.e. 300 ns, 450 ns, 600 ns . . . ) were split up into a corresponding number of pulses having a duration of 150 ns and the same beam current as the respective longer pulse. So for example, the crosses at pulse durations of 600 ns denote the $SNR_{D,S}$ and $SNR_{D,C}$ that are obtained if instead of a single pulse having a pulse duration of 600 ns (and a corresponding beam current such that a dose limit of 1 Gy is obtained), four pulses of a duration of 150 ns and with the same beam current are used. It is clearly seen that the values for $SNR_{D,S}$ and $SNR_{D,C}$ can indeed be significantly increased if the longer pulse is split up into a corresponding number of shorter pulses having an optimized pulse durations.

Figure 13:
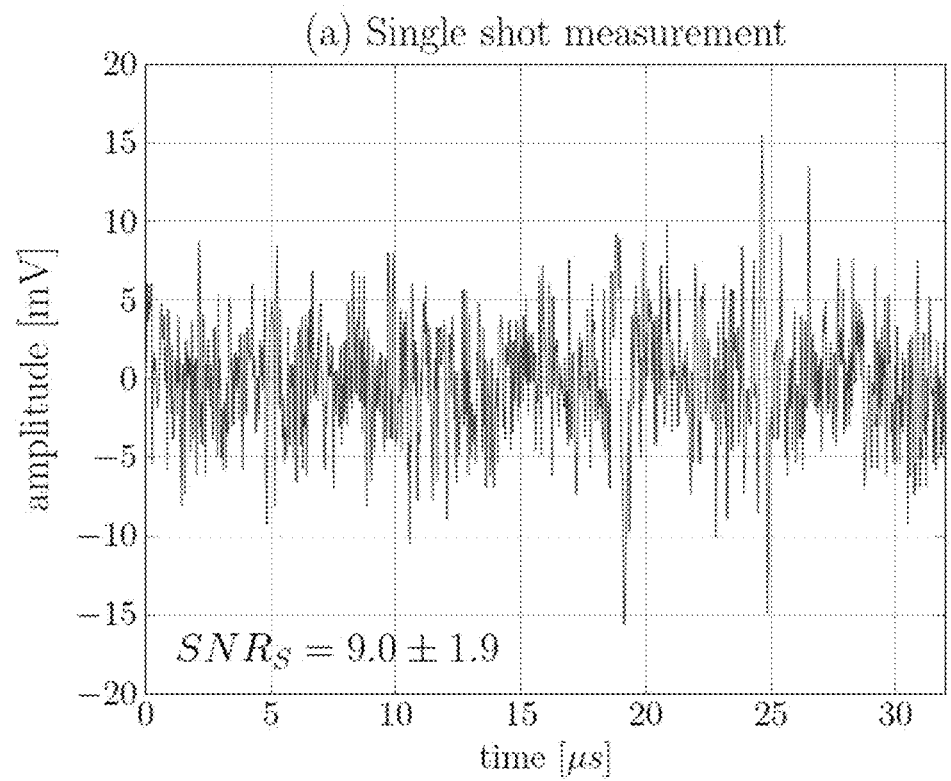
FIG. 13 shows a time-resolved acoustic signal obtained with the system of FIG. 2 applying 20 MeV protons in a water phantom.
Figure 14:
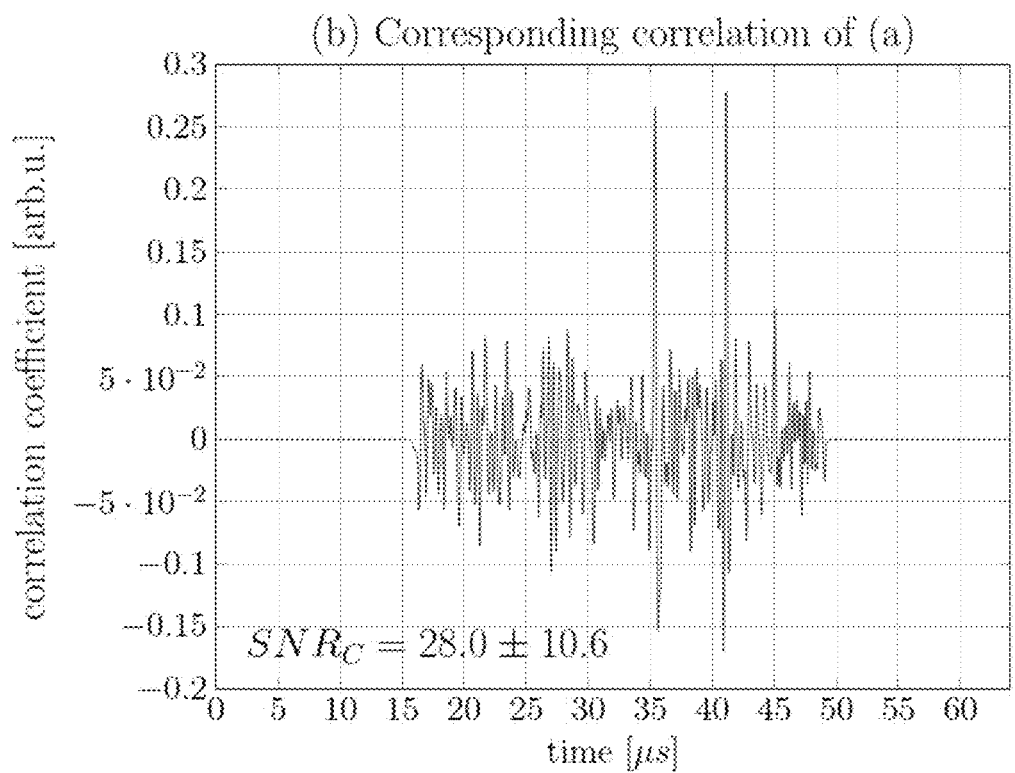
FIG. 14 shows a filtered time-resolved signal generated by 20 MeV protons in a water phantom to which a matched filter has been applied.

A representative single shot measurement and the corresponding correlation function obtained after filtering with the simulated template are shown in FIGS. 13 and 14. FIG. 13 shows a time-resolved acoustic signal obtained with the system of FIG. 2, where 130 ns proton pulse (beam energy 20 MeV) at a beam current of 4.5 µA was used, corresponding to approximately $3.7 \times 10^6$ protons per shot and thus a total peak dose of 0.5 Gy. 200 measurements were carried out, and the signal-to-noise ratio $SNR_S$ of this unfiltered signal, averaged after evaluating every of the independent 200 recorded measurements, amounts to 9.0±1.9.

FIG. 14 shows the filtered time-resolved signal, to which a matched filter based on the above mentioned template has been applied. It is seen that in this case, the signal-to-noise ratio $SNR_C$ of the filtered signal increases to a value of 28.0±10.6. Moreover, within the filtered signal, two peaks can be quite clearly discerned. The first peak corresponds to the signal 1 shown in FIG. 7, i.e. the energy-deposition-signal component attributable to the deposition of the individual pulse in the absorptive medium. The second peak corresponds to the reflection signal shown as signal 3 in FIG. 7.

Since the reflected signal is travelling backwards from the Bragg peak and is being reflected at the entrance window, its delay (also referred to as "time of flight", ToF) compared to the direct signal approximates the time needed for the ultrasound waves to travel twice the range R of the proton beam within the absorptive medium (in this case water). This ToF was determined by calculating the temporal offset between the correlation peak of the direct signals and the reflection signal. The speed of sound in water at the measurement temperature (22.4° C.) is 1482 m/s.

The range R was calculated according to $$R = \frac{v_s \times ToF}{2}$$

for 200 independent measurements. The mean value of the measured ranges is 4.25 mm with a standard deviation of the individual measurements of 0.01 mm and a maximum and minimum range of 4.28 mm and 4.21 mm, respectively. These results show a slight systematic offset when compared with FLUKA Monte Carlo simulations (4.21 mm). However, the maximum deviation between the simulated data and the measured data of 70 µm, which is equal to 1.7% of the full range, shows that the range can be measured accurately using this method.

In this proof of concept experiment, the reflection signal was used in order to calculate the range R. In a realistic clinical setup, however a time of flight method will be used, based on the above mentioned relative timing information of the energy deposition of said individual pulse with respect to said time-resolved acoustic signal, which may typically be determined based on a trigger signal indicating the arrival of a pulse of said pulsed ion beam in the absorptive medium. For this purpose, for example a prompt-γ-trigger may be used, obtained from the protons impinging on the patient as a starting point of the time-of-flight measurement, and the estimated arrival of the ionoacoustic signal ("occurrence timing information") as a stopping point. The resulting time of flight obtained after evaluating the time interval or delay from trigger to the signal arrival will provide information about the distance from the Bragg Peak to the ionoacoustic sensor 24 shown in FIG. 2.

This information is valuable when it is combined with an imaging device positioned at (or right next to) the ionoacoustic sensor 24, such as the ultrasound transducer 22 of FIG. 2. The co-registration of the Bragg peak position within a live ultrasound reveals the relative position of the Bragg peak to the tumor or surrounding organs. While it would in principle be conceivable to incorporate the Bragg beak location within an ultrasound image using the same device as transmitter and receiver, for clinical energies, the low-frequency ionoacoustic signal and the high-frequency ultrasound image will rather need to be recorded with different devices, making a spatial co-registration between the ultrasound device and the ionoacoustic detector necessary.

While the above examples, in which comparatively low beam energies and water as the absorptive medium have been used, can be regarded as proof of concept, the findings can be readily extrapolated to higher, clinically relevant beam energies. This has been confirmed by the inventors by re-evaluating measurements recorded in 2017 at the clinical synchrocyclotron of the Centre Antoine Lacassagne (CAL)

in Nice, France, which were reported in Lehrack et al., Submillimeter ionoacoustic range determination for protons in water at a clinical synchrocyclotron, *Physics in Medicine & Biology*, 62(17): L 20, 2017. For the exact beam characteristics and the experimental setup, reference is made to Lehrack et. al. The acoustic signal of 220 MeV protons was measured for a pulse with a nearly Gaussian shape of 3.7 µs FWHM. In this original study, where no correlation analysis (matched filter) was applied, 1000 consecutive measurements had to be averaged in order to obtain a submillimeter range verification using a ToF method accumulating a total deposited dose at the Bragg peak of roughly 10 Gy. After repeating the 1000-fold measurement five times, a jitter of the maximum position corresponding to a range uncertainty of $\sigma=0.40$ mm was found.

However, applying the matched filter (in this case cross correlation filter) to this data, a similar $SNR_C$ could be achieved using only 13% of the measurements and thus reducing the applied dose to a clinically relevant value of 1.3 Gy. The template used for filtering was generated using the same type of simulations and equations as described above and as applied in the examples above to lower energy case. The main differences compared to the lower energy case is the Gaussian shaped temporal heating function and the significantly broader spatial heating function due to the wider Bragg peak.

FIG. 15 shows the average of 1000 (raw) time-resolved acoustic signals, while FIG. 16 shows the average of only 130 filtered time-resolved signals (correlation functions). The evaluation of seven independent measurement sets of 130 single acquisitions each allowed for the evaluation of the fluctuations of the maximum position of the correlation functions. The statistical range uncertainty was assessed from the jitter of the correlation peaks, where the jitter was calculated as the standard deviation from the mean peak position and is $\Delta t=380$ ns, which corresponds to a range uncertainty of $\Delta R=\pm 0.57$ mm or $\pm 0.19\%$ when compared to the range of the protons of 30.3 cm. Accordingly, it is seen that using clinically relevant doses, at clinically relevant energies, and applying the matched filter to the time-resolved acoustic signal, the location of energy deposition of the ion beam can be determined with submillimeter precision.

Moreover, the findings about the ideal pulse duration discussed in connection with FIG. 9 can also be extrapolated to any proton beam energy being relevant for tumor therapy. The ideal pulse duration can be determined with simulations of ionoacoustic signals generated by increasing pulse durations. This is shown in FIG. 17 for 220 MeV protons including rectangular (dashed) and Gaussian (solid) pulse shapes, for which the pulse duration was chosen to be the FWHM. Similar to FIG. 9, this has been done considering raw measurements of the time-resolved acoustic signal and the corresponding filtered terms of signals (correlation functions) in water with a fixed beam current. Further, the calculated signal power is again normalized by the integral dose of the given pulse duration to ensure a fair comparison ($SNR_D$).

Extending the simulations further, FIG. 18 shows a corridor of preferable pulse durations considering Gaussian pulse shapes and a correlation-based evaluation for all proton energies between 20 MeV and 260 MeV, and FIG. 19 shows a narrower corridor of optimal pulse durations. For the simulations a mono-energetic proton beam and a broadband point transducer in axial position with a large distance to the source was assumed such that the incoming acoustic waves could be approximated as flat. The shaded area in FIG. 18 shows all possible pulse durations for a given energy with which at least 70%, and the shaded area FIG. 19 shows all possible pulse durations for a given energy with which at least 90% of the maximum possible $SNR_{D,C}$ can be reached.

FIGS. 18 and 19 further show the expected central frequencies for the signals generated with these ideal pulse durations on the right γ-axis. The 70% and 90% thresholds within the ideal pulse duration cause a variance in the possible central frequencies which is depicted by the error bars. Because of the increasing range straggling the Bragg curve flattens and widens for increasing beam energies. This causes the increase of the optimal pulse duration for increasing energies and also shifts the frequency content of the ionoacoustic signal to lower frequencies. Note that the frequency spectrum of a single ionoacoustic signal is broadband, so that also frequency components outside the error bars play an important role for ideal detection.

While the present invention has been described in terms of specific embodiments, it is understood that variations and modifications will occur to those in the art, all of which are intended as aspects of the present invention. Accordingly, only such limitations as appear in the claims should be placed on the invention.

REFERENCE CHARACTER LIST

10 ion beam therapy system
12 accelerator
14 ion beam
14' chopped ion beam
16 chopper
18 patient
20 tumor
20' representation of tumor 20 in image on display 32
22 ultrasound transducer
24 ionoacoustic sensor
26 data acquisition unit
28 trigger line
30 control system
32 display
34 indication of location of energy deposition
36 control line
38 database
40 treatment table
42 signal line

What is claimed is:

1. A method of determining information regarding a location of energy deposition of an ion beam in an absorptive medium, comprising the following steps:
    generating a pulsed ion beam,
    detecting a time-resolved acoustic signal, said time-resolved acoustic signal comprising an energy-deposition-signal component attributable to the energy deposition of an individual pulse of said pulsed ion beam in said absorptive medium,
    determining relative timing information of the energy deposition of said individual pulse with respect to said time-resolved acoustic signal,
    providing a matched filter for processing the time-resolved acoustic signal, said matched filter being configured to facilitate detecting said energy-deposition-signal component within said time-resolved acoustic signal,
    applying said matched filter to said time-resolved acoustic signal to thereby obtain a filtered time-resolved signal,
    deriving, from said filtered time-resolved signal, occurrence timing information related to an occurrence of said energy-deposition signal component in said time-resolved acoustic signal, and deriving information regarding the location of the energy deposition based, at least in part, on a delay between said energy deposition of said individual pulse and said occurrence timing information.

2. The method of claim 1, wherein said absorptive medium is a tissue of a patient undergoing radiation therapy.

3. The method of claim 1, wherein said step of providing the matched filter comprises providing a template, said template representing a predicted waveform of the energy-deposition-signal component.

4. The method of claim 3, wherein applying said matched filter to said time-resolved acoustic signal comprises correlating said template with said time-resolved acoustic signal, or convolving the time-resolved acoustic signal with a conjugated time-reversed version of the template.

5. The method of claim 3, wherein the step of providing said template comprises determining the template at least in part by computer simulation, wherein said simulation comprises simulating the template as an ionoacoustic signal caused by an estimated time-dependent energy deposition distribution of the ion beam in said absorptive medium.

6. The method of claim 5, further comprising a step of obtaining said estimated time-dependent energy deposition by computer simulation as well.

7. The method of claim 5, wherein said simulation of said template by said ionoacoustic signal is based on space-resolved information about mass density and/or speed of sound in a tissue of a patient, and the space-resolved information is obtained from medical images obtained during one or both of a treatment planning and during radiation therapy.

8. The method of claim 3, wherein said step of providing said template further comprises accounting for transducer characteristics of a transducer used for detecting the time-resolved acoustic signal, wherein the transducer characteristics are accounted for using a transfer function associated with said transducer, or a bandpass filter approximating the transducer's transfer function.

9. The method of claim 3, wherein said step of providing said template comprises optimizing the template in an iterative procedure, to thereby increase the signal-to-noise ratio (SNR) of the filtered time resolved signal.

10. The method of claim 3, wherein providing said template comprises selecting one or more templates from a database of previously generated templates, wherein said previously generated templates comprise templates which are, at least in part, based on energy-deposition-signal components obtained by experiment using doses higher than 40 Gy.

11. The method of claim 10, wherein said one or more selected templates are further modified to account for one or both of a shape of the individual pulse and the characteristics of a sensor used for detecting the time-resolved acoustic signal.

12. The method of claim 1, wherein said relative timing information of the energy deposition of said individual pulse with respect to said time-resolved acoustic signal is determined based on a trigger signal indicating an arrival of a pulse of said pulsed ion beam in the absorptive medium, wherein said trigger signal is one of
an electric signal provided by electronic components involved with generating said pulsed ion beam,
a signal provided by a detector provided in front of the absorptive medium, and
a signal provided by a detector for detecting secondary radiation due to an interaction of the ion beam with the absorptive medium.

13. The method of claim 1, wherein said time-resolved acoustic signal is detected using at least one detection apparatus,
wherein said at least one detection apparatus comprises an ionoacoustic transducer for detecting said time-resolved acoustic signal, and wherein
said ionoacoustic transducer is adapted to record ultrasonic images of said absorptive medium as well, or
wherein an ultrasound transducer is provided in a known spatial relationship to said ionoacoustic transducer.

14. The method of claim 13, wherein said location of the energy deposition is derived with respect to a coordinate system associated with an ultrasound image recorded with said ionoacoustic transducer or with said ultrasound transducer in said known spatial relationship to said ionoacoustic transducer further comprising a step of providing a medical image in which said location of energy deposition is indicated, wherein said medical image is one of said ultrasound image, an image derived from said ultrasound image, and a medical image acquired with an imaging modality different from ultrasound imaging that is co-registered with said ultrasound image.

15. The method of claim 14, wherein a target area for energy deposition according to a treatment plan is associated with said medical image, said method further comprising a step of determining whether the location of energy deposition with regard to said target area deviates from said treatment plan, and in case the deviation exceeds a predetermined threshold, deriving control or operating parameters such as to decrease the deviation, wherein the control or operating parameters relate to energy of the ion beam or to positioning parameters for a treatment table on which a patient is placed.

16. The method of claim 1, wherein the ions are protons, and a pulse duration $t_d$ given as the full width at half maximum (FWHM) of a Gaussian fitted in a least square fit to an actual pulse shape is chosen as a function of proton energy $E_P$, such that $$f(E_P) \leq t_d \leq g(E_P),$$

wherein $t_d$ is measured in µs, $E_P$ is measured in MeV and chosen from a range between 20 MeV and 260 MeV, and $f(E_P)$, $g(E_P)$ are second order polynomials defined as $$f(E_P) = p1(E_P)^2 + p2\, E_P + p3 \text{ and}$$

$$g(E_P) = q1(E_P)^2 + q2\, E_P + q3, \text{ respectively,}$$

wherein the coefficients $p_i$ and $q_i$ with i=1 ... 3 are chosen as follows:
p1=1.476*10$^{-5}$, p2=0.002486, p3=−0.05185, and
q1=0.000118, q2=0.03548, q3=−0.9488.

17. The method of claim 16, wherein for a given dose limit of protons of proton energy $E_P$ to be irradiated into tissue of a patient, the dose is split into two or more pulses, each of which, have a pulse duration $t_d$.

18. An apparatus for determining information regarding the location of energy deposition of a pulsed ion beam in an absorptive medium, said apparatus comprising:
a detection apparatus for detecting a time-resolved acoustic signal, said time-resolved acoustic signal comprising an energy-deposition-signal component attributable to the energy deposition of an individual pulse of a pulsed ion beam in said absorptive medium, a device for determining relative timing information of the energy deposition of said individual pulse with respect to said time-resolved acoustic signal, and a control system, said control system configured for applying a matched filter to said time-resolved acoustic signal to thereby obtain a filtered time-resolved signal, said matched filter being configured to facilitate detecting said energy-deposition-signal component within said time-resolved acoustic signal, deriving, from said filtered time-resolved signal, occurrence timing information related to the occurrence of said energy-deposition signal component in said time-resolved acoustic signal, and deriving information regarding the location of the energy deposition based, at least in part, on a delay between said energy deposition of said individual pulse and said occurrence timing information.

19. The apparatus of claim 18, wherein the device for determining relative timing information of the energy deposition of said individual pulse with respect to said time-resolved acoustic signal utilizes a trigger signal indicating the arrival of a pulse of said pulsed ion beam in the absorptive medium, wherein said trigger signal is one of an electric signal provided by electronic components involved with generating said pulsed ion beam, a signal provided by a detector provided in front of the absorptive medium, and a signal provided by a detector for detecting secondary radiation due to the interaction of the ion beam with the absorptive medium.

20. The apparatus of 18, wherein said at least one detection apparatus comprises an ionoacoustic transducer for detecting said time-resolved acoustic signal, and wherein said ionoacoustic transducer is adapted to record ultrasonic images of said absorptive medium as well, or wherein said apparatus further comprises an ultrasound transducer in a defined spatial relationship to said ionoacoustic transducer.

* * * * *